(12) United States Patent
Rosenberg et al.

(10) Patent No.: US 8,401,645 B2
(45) Date of Patent: *Mar. 19, 2013

(54) ELECTRODE AND LEAD STABILITY INDEXES AND STABILITY MAPS BASED ON LOCALIZATION SYSTEM DATA

(75) Inventors: Stuart Rosenberg, Castaic, CA (US); Thao Thu Nguyen, Bloomington, MN (US); Kyungmoo Ryu, Palmdale, CA (US); Kjell Norén, Solna (SE); Allen Keel, San Francisco, CA (US); Wenbo Hou, Lancaster, CA (US); Michael Yang, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 471 days.

This patent is subject to a terminal disclaimer.

(21) Appl. No.: 12/562,003

(22) Filed: Sep. 17, 2009

(65) Prior Publication Data

US 2011/0066201 A1  Mar. 17, 2011

(51) Int. Cl.
*A61N 1/00* (2006.01)
*A61B 5/04* (2006.01)

(52) U.S. Cl. .............. 607/28; 600/510; 607/9

(58) Field of Classification Search .......... 600/510; 607/9, 14, 27–28
See application file for complete search history.

(56) References Cited

U.S. PATENT DOCUMENTS

| | | | |
|---|---|---|---|
| 5,848,972 A * | 12/1998 | Triedman et al. | 600/508 |
| 6,584,345 B2 * | 6/2003 | Govari | 600/509 |
| 6,941,166 B2 * | 9/2005 | MacAdam et al. | 600/521 |
| 6,996,434 B2 * | 2/2006 | Marcovecchio et al. | 600/509 |
| 7,082,330 B2 | 7/2006 | Stadler et al. | |
| 7,505,810 B2 * | 3/2009 | Harlev et al. | 600/509 |
| 7,529,584 B2 * | 5/2009 | Laske et al. | 607/9 |
| 7,613,500 B2 | 11/2009 | Vass et al. | |
| 2007/0135721 A1 | 6/2007 | Zdeblick | |
| 2008/0058656 A1 | 3/2008 | Costello et al. | |
| 2008/0183072 A1 | 7/2008 | Robertson et al. | |
| 2008/0242976 A1 | 10/2008 | Robertson et al. | |
| 2009/0018632 A1 | 1/2009 | Zdeblick et al. | |
| 2009/0093857 A1 | 4/2009 | Markowitz et al. | |
| 2010/0152801 A1 * | 6/2010 | Koh et al. | 607/9 |
| 2011/0066202 A1 * | 3/2011 | Rosenberg et al. | 607/17 |
| 2011/0066203 A1 * | 3/2011 | Rosenberg et al. | 607/17 |
| 2011/0092809 A1 * | 4/2011 | Nguyen et al. | 600/424 |

FOREIGN PATENT DOCUMENTS

| | | |
|---|---|---|
| WO | 2006105394 A1 | 10/2006 |
| WO | 2007111542 A1 | 10/2007 |
| WO | 2009009746 A1 | 1/2009 |

* cited by examiner

*Primary Examiner* — Christopher D Koharski
*Assistant Examiner* — Catherine Voorhees

(57) ABSTRACT

A method includes selecting an electrode located in a patient; acquiring position information with respect to time for the electrode where the acquiring uses the electrode for repeatedly measuring electrical potentials in an electrical localization field established in the patient; calculating a stability metric for the electrode based on the acquired position information with respect to time; and deciding if the selected electrode, as located in the patient, has a stable location for sensing biological electrical activity, for delivering electrical energy or for sensing biological electrical activity and delivering electrical energy. Position information may be acquired during one or both of intrinsic or paced activation of a heart and respective stability indexes calculated for each activation type.

25 Claims, 15 Drawing Sheets

EXEMPLARY METHOD 900

POSITION INFORMATION 905

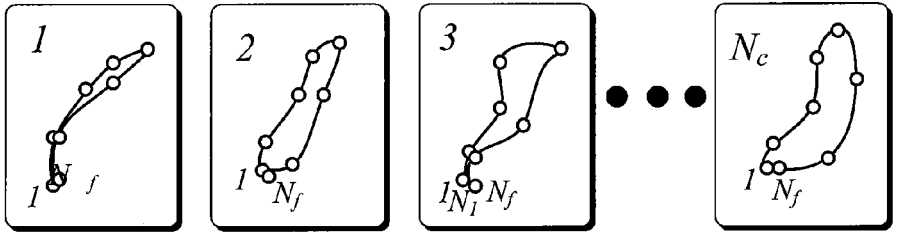

STABILITY INDEX SUM EQUATION 910

$$SI_{sum} = \frac{1}{N_c} \sum_{j=1}^{N_c} \sum_{i=1}^{N_f} \left| \vec{X}_i^j - \vec{X}_i^0 \right|$$

STABILITY INDEX MEAN EQUATION 920

$$SI_{mean} = \frac{1}{N_c N_f} \sum_{j=1}^{N_c} \sum_{i=1}^{N_f} \left| \vec{X}_i^j - \vec{X}_i^0 \right|$$

STABILITY INDEX STD. DEV. EQUATION 930

$$SI_{stddev} = \sqrt{\frac{1}{N_c - 1} \left[ \sum_{j=1}^{N_c} \left( L_j - \frac{1}{N_c} \sum_{j=1}^{N_c} L_j \right)^2 \right]}$$

FIG. 9

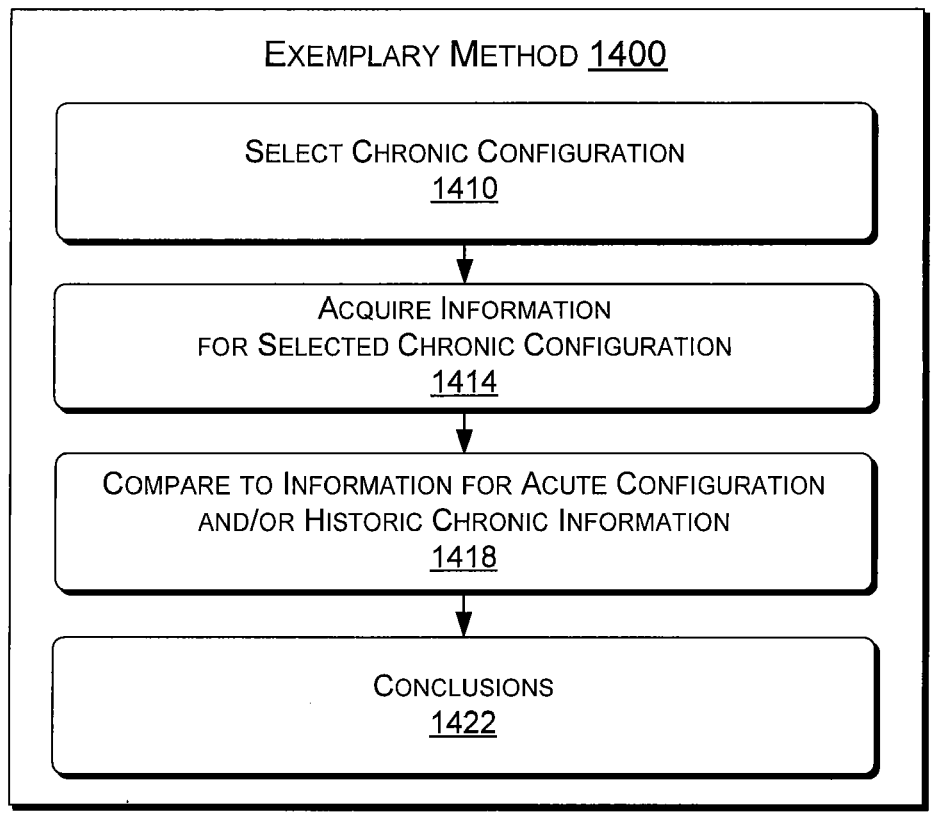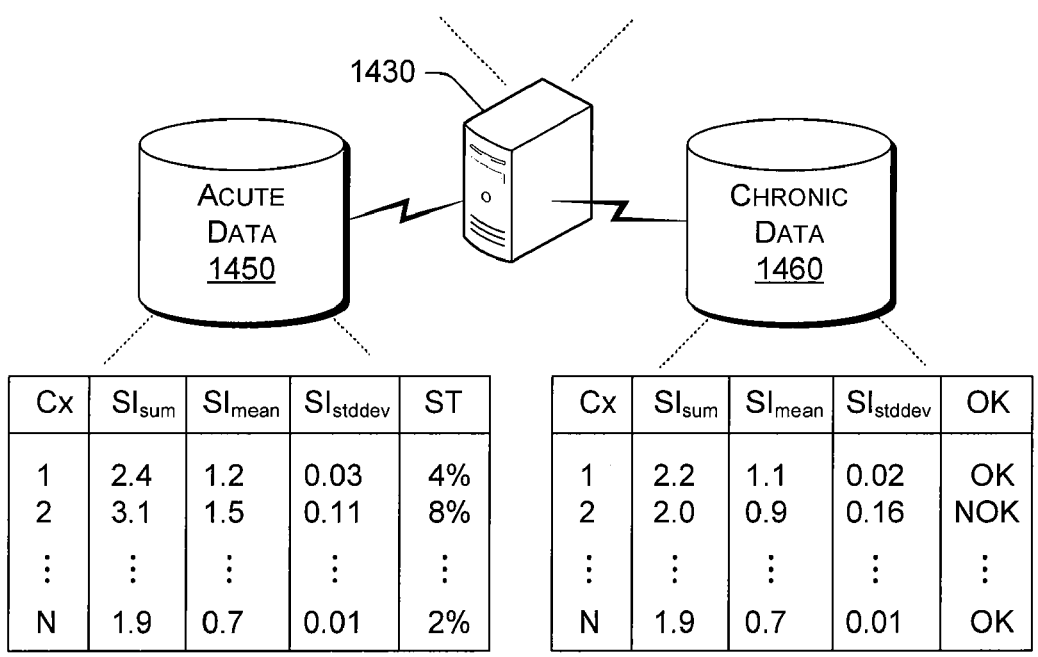
FIG. 14

ELECTRODE AND LEAD STABILITY INDEXES AND STABILITY MAPS BASED ON LOCALIZATION SYSTEM DATA

This application is related to U.S. patent application:

1) Ser. No. 12/562,007, filed concurrently herewith, titled "Electrode and Lead Stability Indexes and Stability Maps Based on Localization System Data"; and 2) Ser. No. 12/562,018, filed concurrently herewith, titled "Electrode and Lead Stability Indexes and Stability Maps Based on Localization System Data".

TECHNICAL FIELD

Subject matter presented herein relates generally to electrode and lead-based investigation or therapy systems (e.g., cardiac pacing therapies, cardiac stimulation therapies, etc.). Various examples acquire position data using a localization system and, based on the acquired data, calculate stability metrics (e.g., as indexes or maps).

BACKGROUND

Various surgical procedures rely on placement of electrodes into the body (e.g., electrode devices, electrode-bearing leads or catheters, etc.). For example, a typical implantable cardiac defibrillator (ICD) includes a "can" for placement in a pectoral pocket and an electrode-bearing lead for placement into a chamber of the heart or a vein of the heart. In this example, an electrode of the can and an electrode of the lead can sense cardiac electrical activity indicative of fibrillation and respond (e.g., by control logic in the can) by delivering energy to defibrillate the heart. To ensure proper performance, whether for sensing or for defibrillating, stability of the can and stability of the lead are beneficial.

In another example, where a patient is treated by a cardiac resynchronization therapy (CRT) device that relies on biventricular pacing, an electrode-bearing lead may be placed into the right ventricle and another electrode-bearing lead may be placed in a vein of a wall of the left ventricle. As the algorithms for delivery of such therapy become more complex, accurate sensing becomes more important as does an ability to accurately and reproducibly deliver pacing stimuli. In this example, stability of sensing and pacing electrodes becomes quite important.

In either example, where an electrode or lead lacks stability or dislodges, depending on the severity, surgery may be required to remedy the issue. Alternatively, if the lack of stability or the dislodgement is tolerated, a device's ability to delivery therapy in an optimal manner may be compromised (e.g., an electrode configuration for sensing may become unreliable to support an algorithm such as for automatic determination of capture threshold).

While many leads include anchoring mechanisms, such mechanisms do not guarantee stability. However, if a lead can be placed in a stable location or a location of known stability, a clinician can predict better possible outcomes and even longevity of an implantable therapy device. As to the latter, data indicates that an unstable electrode is likely to trigger algorithms such as an automatic capture threshold determination algorithm, which, in turn, can consume precious resources (e.g., consider a battery as an implantable device's limited power supply).

While ICD and CRT have been mentioned, electrode and lead stability can be an issue with other investigations or procedures. For example, consider an ablation procedure in a region of the heart that may be accessed via two different catheter paths. If one of the paths proves for more stable placement of an ablation instrument (e.g., electrode, RF, chemical, etc.), the clinician may perform the procedure with less risk and perhaps a better clinical outcome. In another example, consider nerve or tissue stimulation therapies such as those for vagal nerve stimulation or for diaphragm stimulation. These therapies can benefit from known, trackable or otherwise quantifiable stability metrics. In yet another example, consider placement of a sensor in the body that may require stability for suitable signal-to-noise.

As described herein, various exemplary techniques can assess stability in acute states and optionally chronic states. As explained, such stability information can be beneficial in aiding a clinician to make decisions regarding an investigation or a therapy.

SUMMARY

An exemplary method includes selecting an electrode located in a patient; acquiring position information with respect to time for the electrode where the acquiring uses the electrode for repeatedly measuring electrical potentials in an electrical localization field established in the patient; calculating a stability metric for the electrode based on the acquired position information with respect to time; and deciding if the selected electrode, as located in the patient, has a stable location for sensing biological electrical activity, for delivering electrical energy or for sensing biological electrical activity and delivering electrical energy. Various other methods, devices, systems, etc., are also disclosed.

Another exemplary method includes selecting an electrode located in a patient wherein the electrode comprises a lead-based electrode; acquiring position information with respect to time for the electrode, during both loaded and unloaded conditions of the lead, where the acquiring uses the electrode for repeatedly measuring electrical potentials in an electrical localization field established in the patient; calculating both loaded and unloaded stability metrics for the electrode based on the acquired position information with respect to time; and comparing the unloaded and loaded stability metrics to decide whether the electrode, as located in the patient, comprises a stable location for delivery of therapy.

Another exemplary method includes selecting an electrode located in a patient; acquiring position information with respect to time for the electrode, during both acute and chronic states of the electrode, where the acquiring uses the electrode for repeatedly measuring electrical potentials in an electrical localization field established in the patient; calculating an acute state stability metric and a chronic state stability metric for the electrode based on the acquired position information with respect to time; and comparing the acute state stability metric to the chronic state stability metric to decide whether the electrode, as located in the patient in the chronic state, comprises a stable location for delivery of a therapy. The chronic state stability metric of an electrode may be monitored over time to decide whether stability of the electrode has changed.

BRIEF DESCRIPTION OF THE DRAWINGS

Features and advantages of the described implementations can be more readily understood by reference to the following description taken in conjunction with the accompanying drawings.

FIG. 9 is a block diagram of an exemplary method for determining various stability indexes based on position information of an electrode acquired over multiple cardiac cycles.

FIG. 14 is a block diagram of an exemplary method for acquiring position information during a chronic state and comparing chronic state information to acute state information or previously acquired (e.g., historic) chronic state information to thereby assess stability of one or more electrodes or leads.

DETAILED DESCRIPTION

Figure 1:
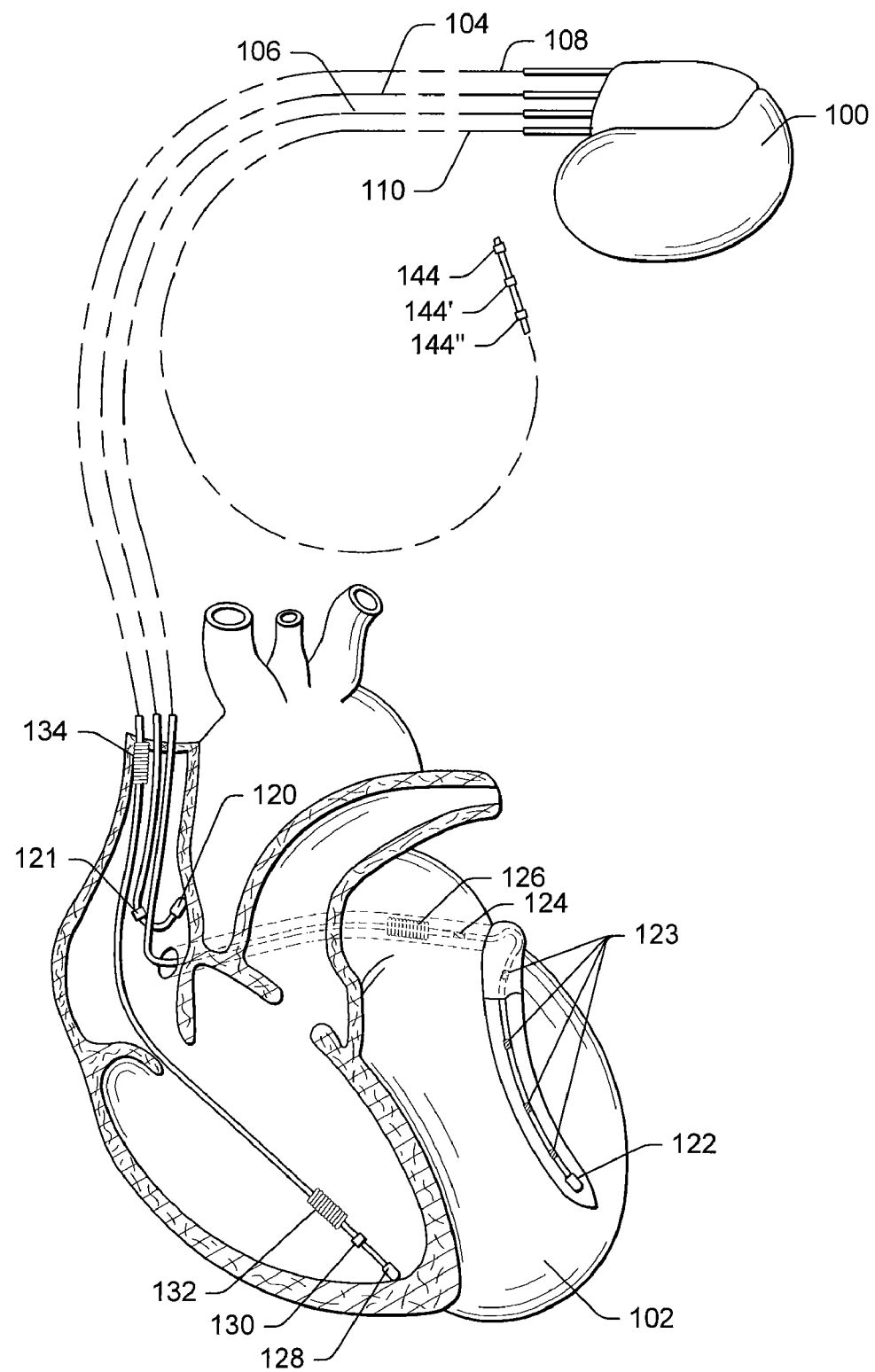
FIG. 1 is a simplified diagram illustrating an exemplary implantable stimulation device in electrical communication with at least three leads implanted into a patient's heart and at least one other lead for sensing and/or delivering stimulation and/or shock therapy. Other devices with more or fewer leads may also be suitable.

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators are typically used to reference like parts or elements throughout.

Overview

Various exemplary techniques described herein pertain to stability analysis of electrodes or lead in the body. For example, during an intraoperative procedure, a clinician may maneuver a catheter to various locations in one or more chambers or vessels of the heart and acquire position information sufficient to calculate one or more stability metrics. In various examples, acquisition of position information may occur for a chronic state, for example, sufficient to calculated one or more chronic state stability metrics.

Various exemplary methods may be implemented, for example, using a pacing system analyzer (PSA) and a localization system or a specialized localization system. Various examples are described with respect to the ENSITE® NAVX® localization system; noting that other types of localization systems may be used.

Various techniques aim to facilitate lead implants, particularly for leads that enter the coronary sinus to reach distal branches thereof. For example, a clinician can view a map of stability metrics and readily decide to locate a lead in a region with appropriate stability, whether for sensing or pacing. A typical intraoperative, acute state process occurs iteratively (i.e., select or move, acquire, calculate; select or move, acquire, calculate; . . . ). In this iterative process, a clinician may note whether a location is of acceptable stability or of unacceptable stability.

As described herein, various techniques can calculate stability metrics and generate maps. Various techniques may operate in conjunction with one or more PSA functionalities, for example, to create and display maps that show variations in stability metrics with respect to anatomic features.

As described herein, various exemplary techniques can be used to make decisions as to cardiac pacing therapy and optimization of a cardiac pacing therapy (e.g., CRT or other pacing therapies). In a clinical trial, acute resynchronization was shown to be a significant factor in assessing CRT efficacy and long-term outcome[1]. Various methods described herein, build on this clinical finding by formulating specialized techniques and stability metrics associated with locations for pacing and sensing. In turn, a clinician can assess how a particular CRT therapy or configuration thereof may be expected to perform at time of implant or, in some instances, after implant.

[1] G B Bleeker, S A Mollema, E R Holman, N Van De Veire, C Ypenburg, E Boersma, E E van der Wall, M J Schalij, J J Bax. "Left Ventricular Resynchronization is Mandatory for Response to Cardiac Resynchronization Therapy: Analysis in Patients with Echocardiographic Evidence of Left Ventricular Dyssynchrony at Baseline". *Circulation* 2007; 116: 1440-1448.

An exemplary stimulation device is described followed by various techniques for acquiring and calculating stability metrics. The drawings and detailed description elucidate details of various distinct stability metrics that may be used singly or in combination during an assessment or an optimization process (e.g., acute or chronic).

Exemplary Device

The techniques described below are intended to be implemented in connection with any device that is configured or configurable to delivery cardiac therapy and/or sense information germane to cardiac therapy.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of nerves or other tissue. In addition, the device 100 includes a fourth lead 110 having, in this implementation, three electrodes 144, 144', 144" suitable for stimulation and/or sensing of physiologic signals. This lead may be positioned in and/or near a patient's heart and/or remote from the heart.

The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation and/or sensing.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

In the example of FIG. 1, the coronary sinus lead 106 includes a series of electrodes 123. In particular, a series of four electrodes are shown positioned in an anterior vein of the heart 102. Other coronary sinus leads may include a different number of electrodes than the lead 106. As described herein, an exemplary method selects one or more electrodes (e.g., from electrodes 123 of the lead 106) and determines characteristics associated with conduction and/or timing in the heart to aid in ventricular pacing therapy and/or assessment of cardiac condition. As described in more detail below, an illustrative method acquires information using various electrode configurations where an electrode configuration typically includes at least one electrode of a coronary sinus lead or other type of left ventricular lead. Such information may be used to determine a suitable electrode configuration for the lead 106 (e.g., selection of one or more electrodes 123 of the lead 106).

An exemplary coronary sinus lead 106 can be designed to receive ventricular cardiac signals (and optionally atrial signals) and to deliver left ventricular pacing therapy using, for example, at least one of the electrodes 123 and/or the tip electrode 122. The lead 106 optionally allows for left atrial pacing therapy, for example, using at least the left atrial ring electrode 124. The lead 106 optionally allows for shocking therapy, for example, using at least the left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference.

The stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating other tissue; such an electrode may be positioned on the lead or a bifurcation or leg of the lead. A right ventricular lead may include a series of electrodes, such as the series 123 of the left ventricular lead 106.

Figure 2:
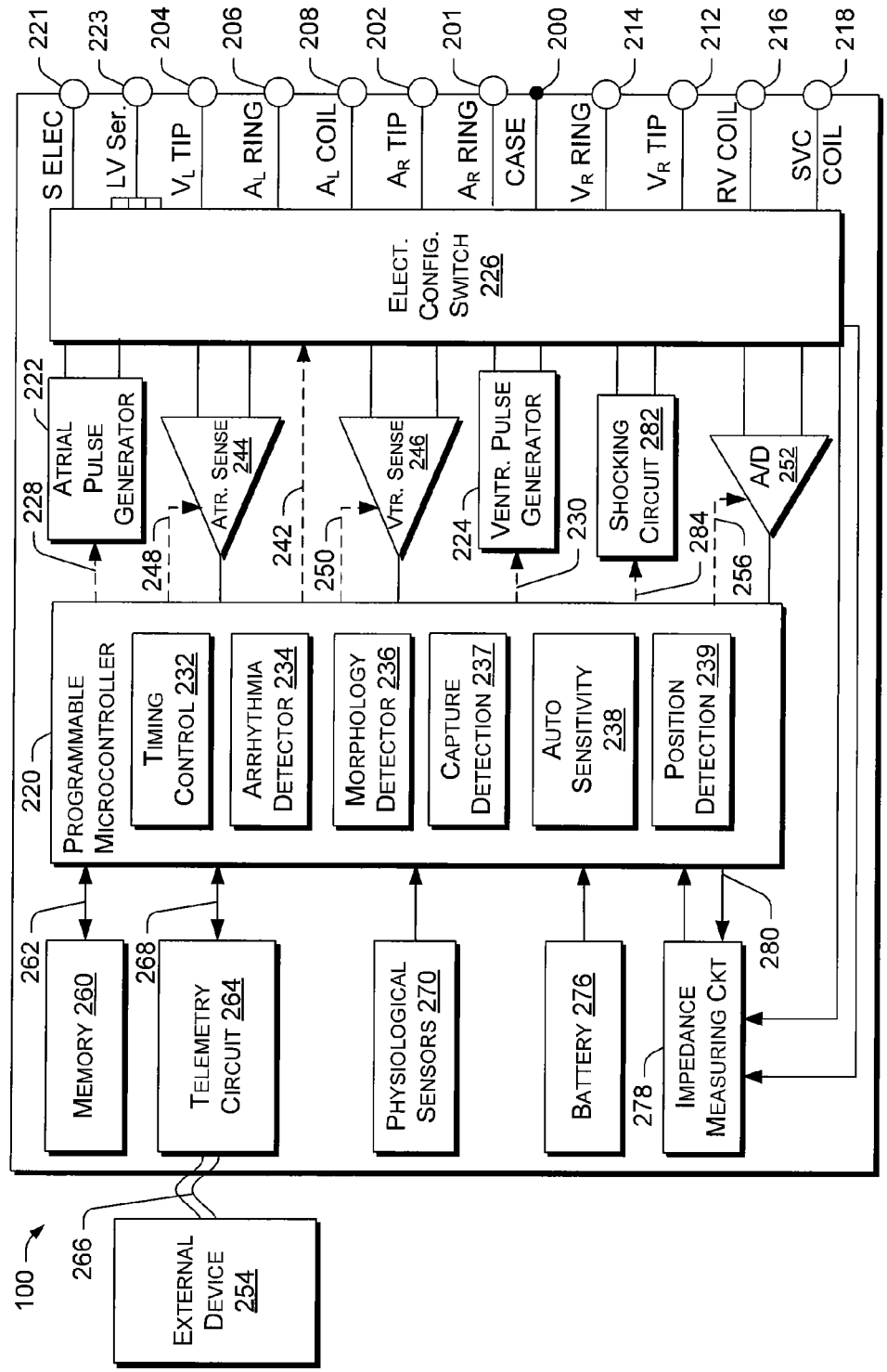
FIG. 2 is a functional block diagram of an exemplary implantable stimulation device illustrating basic elements that are configured to provide cardioversion, defibrillation, pacing stimulation and/or other tissue stimulation. The implantable stimulation device is further configured to sense information and administer therapy responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques, methods, etc., described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart.

Housing 200 for the stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking or other purposes. Housing 200 further includes a connector (not shown) having a plurality of terminals 201, 202, 204, 206, 208, 212, 214, 216, 218, 221, 223 (shown schematically and, for convenience, the names of the electrodes to which they are connected are shown next to the terminals).

To achieve right atrial sensing, pacing and/or other stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable stimulation electrodes is also possible via these and/or other terminals (e.g., via a stimulation terminal S ELEC 221). The terminal S ELEC 221 may optionally be used for sensing. For example, electrodes of the lead 110 may connect to the device 100 at the terminal 221 or optionally at one or more other terminals.

A terminal 223 allows for connection of a series of left ventricular electrodes. For example, the series of four electrodes 123 of the lead 106 may connect to the device 100 via the terminal 223. The terminal 223 and an electrode configuration switch 226 allow for selection of one or more of the series of electrodes and hence electrode configuration. In the example of FIG. 2, the terminal 223 includes four branches to the switch 226 where each branch corresponds to one of the four electrodes 123.

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of cardiac or other therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that is suitable to carry out the functions described herein. The use of microprocessor-based control circuits for performing timing and data analysis functions are well known in the art. As described herein, the microcontroller 220 operates according to control logic, which may be in the form of hardware, software (including firmware) or a combination of hardware and software. With respect to software, control logic instructions may be stored in memory (e.g., memory 260) for execution by the microcontroller 220 to implement control logic.

Representative types of control circuitry that may be used in connection with the described embodiments can include the microprocessor-based control system of U.S. Pat. No. 4,940,052, the state-machine of U.S. Pat. Nos. 4,712,555 and 4,944,298, all of which are incorporated by reference herein. For a more detailed description of the various timing intervals used within the stimulation device and their inter-relationship, see U.S. Pat. No. 4,788,980, also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, interatrial conduction (AA) delay, or interventricular conduction (VV) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234. The detector 234 can be utilized by the stimulation device 100 for determining desirable times to administer various therapies. The detector 234 may be implemented in hardware as part of the microcontroller 220, or as software/firmware instructions programmed into the device and executed on the microcontroller 220 during certain modes of operation.

Microcontroller 220 further includes a morphology discrimination module 236, a capture detection module 237 and an auto sensing module 238. These modules are optionally used to implement various exemplary recognition algorithms and/or methods presented below. The aforementioned components may be implemented in hardware as part of the microcontroller 220, or as software/firmware instructions programmed into the device and executed on the microcontroller 220 during certain modes of operation. The capture detection module 237, as described herein, may aid in acquisition, analysis, etc., of information relating to IEGMs and, in particular, act to distinguish capture versus non-capture versus fusion.

The microcontroller 220 further includes an optional position detection module 239. The module 239 may be used for purposes of acquiring position information, for example, in conjunction with a device (internal or external) that may use body surface patches or other electrodes (internal or external). The microcontroller 220 may initiate one or more algorithms of the module 239 in response to a signal detected by various circuitry or information received via the telemetry circuit 264. Instructions of the module 239 may cause the device 100 to measure potentials using one or more electrode configurations where the potentials correspond to a potential field generated by current delivered to the body using, for example, surface patch electrodes. Such a module may help monitor position and cardiac mechanics in relationship to cardiac electrical activity and may help to optimize cardiac resynchronization therapy. The module 239 may operate in conjunction with various other modules and/or circuits of the device 100 (e.g., the impedance measuring circuit 278, the switch 226, the A/D 252, etc.).

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial and ventricular sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 may utilize the atrial and ventricular sensing circuits, 244 and 246, to sense cardiac signals to determine whether a rhythm is physiologic or pathologic. Of course, other sensing circuits may be available depending on need and/or desire. In reference to arrhythmias, as used herein, "sensing" is reserved for the noting of an electrical signal or obtaining data (information), and "detection" is the processing (analysis) of these sensed signals and noting the presence of an arrhythmia or of a precursor or other factor that may indicate a risk of or likelihood of an imminent onset of an arrhythmia.

The exemplary detector module 234, optionally uses timing intervals between sensed events (e.g., P-waves, R-waves, and depolarization signals associated with fibrillation which are sometimes referred to as "F-waves") and to perform one or more comparisons to a predefined rate zone limit (i.e., bradycardia, normal, low rate VT, high rate VT, and fibrillation rate zones) and/or various other characteristics (e.g., sudden onset, stability, physiologic sensors, and morphology, etc.) in order to determine the type of remedial therapy (e.g., anti-arrhythmia, etc.) that is desired or needed (e.g., bradycardia pacing, anti-tachycardia pacing, cardioversion shocks or defibrillation shocks, collectively referred to as "tiered therapy"). Similar rules can be applied to the atrial channel to determine if there is an atrial tachyarrhythmia or atrial fibrillation with appropriate classification and intervention.

Figure 11:
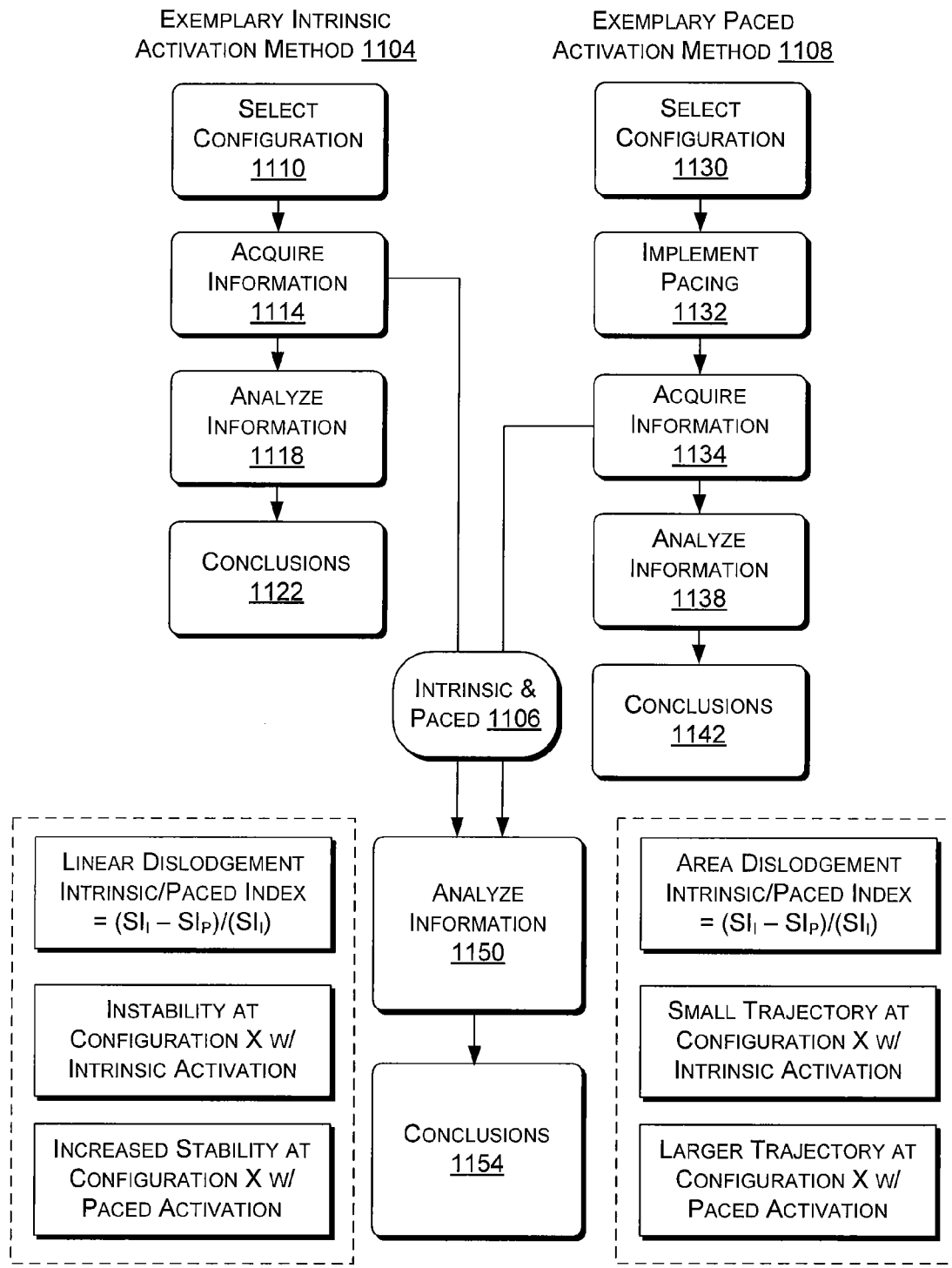
FIG. 11 is a block diagram of an exemplary method for stability analysis of position information acquired during intrinsic activation of the heart and position information acquired during paced activation of the heart.

Cardiac signals are also applied to inputs of an analog-to-digital (A/D) data acquisition system 252. Additional configurations are shown in FIG. 11 and described further below. The data acquisition system 252 is configured to acquire intracardiac electrogram (IEGM) signals or other action potential signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes. A control signal 256 from the microcontroller 220 may instruct the A/D 252 to operate in a particular mode (e.g., resolution, amplification, etc.).

Various exemplary mechanisms for signal acquisition are described herein that optionally include use of one or more analog-to-digital converter. Various exemplary mechanisms allow for adjustment of one or more parameter associated with signal acquisition.

The microcontroller 220 is further coupled to a memory 260 by a suitable data/address bus 262, where the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms (IEGM) and other information (e.g., status information relating to the operation of the device 100, etc., as contained in the microcontroller 220 or memory 260) to be sent to the external device 254 through an established communication link 266.

The stimulation device 100 can further include one or more physiologic sensors 270. For example, the device 100 may include a "rate-responsive" sensor that may provide, for example, information to aid in adjustment of pacing stimulation rate according to the exercise state of the patient. However, the one or more physiological sensors 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses.

While shown as being included within the stimulation device 100, it is to be understood that one or more of the physiologic sensors 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, and so forth. Another sensor that may be used is one that detects activity variance, where an activity sensor is monitored diurnally to detect the low variance in the measurement corresponding to the sleep state. For a complete description of the activity variance sensor, the reader is directed to U.S. Pat. No. 5,476,483 which is hereby incorporated by reference.

The one or more physiological sensors 270 optionally include sensors for detecting movement and minute ventilation in the patient. Signals generated by a position sensor, a MV sensor, etc., may be passed to the microcontroller 220 for analysis in determining whether to adjust the pacing rate, etc. The microcontroller 220 may monitor the signals for indications of the patient's position and activity status, such as whether the patient is climbing upstairs or descending downstairs or whether the patient is sitting up after lying down.

The stimulation device 100 additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (e.g., corresponding to thresholds in the range of approximately 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

As already mentioned, the implantable device 100 includes impedance measurement circuitry 278. Such a circuit may measure impedance or electrical resistance through use of various techniques. For example, the device 100 may deliver a low voltage (e.g., about 10 mV to about 20 mV) of alternating current between the RV tip electrode 128 and the case electrode 200. During delivery of this energy, the device 100 may measure resistance between these two electrodes where the resistance depends on any of a variety of factors. For example, the resistance may vary inversely with respect to volume of blood along the path.

In another example, resistance measurement occurs through use of a four terminal or electrode technique. For example, the exemplary device 100 may deliver an alternating current between one of the RV tip electrode 128 and the case electrode 200. During delivery, the device 100 may measure a potential between the RA ring electrode 121 and the RV ring electrode 130 where the potential is proportional to the resistance between the selected potential measurement electrodes.

With respect to two terminal or electrode techniques, where two electrodes are used to introduce current and the same two electrodes are used to measure potential, parasitic electrode-electrolyte impedances can introduce noise, especially at low current frequencies; thus, a greater number of terminals or electrodes may be used. For example, aforementioned four electrode techniques, where one electrode pair introduces current and another electrode pair measures potential, can cancel noise due to electrode-electrolyte interface impedance. Alternatively, where suitable or desirable, a two terminal or electrode technique may use larger electrode areas (e.g., even exceeding about 1 $cm^2$) and/or higher current frequencies (e.g., above about 10 kHz) to reduce noise.

Figure 3:
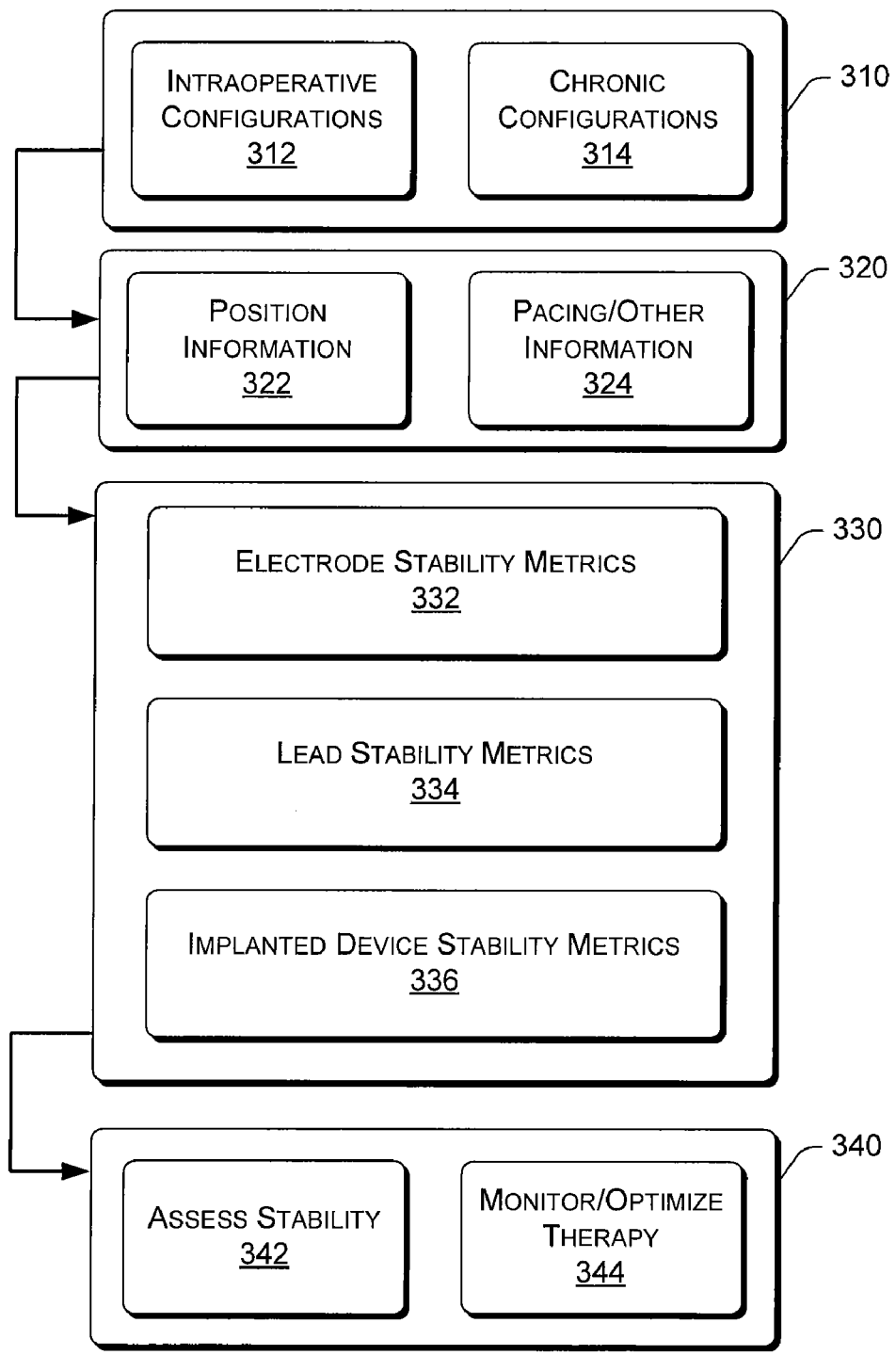
FIG. 3 is a block diagram of an exemplary method for selecting one or more configurations, optimizing therapy and/or monitoring conditions based at least in part on one or more stability metrics.

FIG. 3 shows an exemplary method 300 for acquiring position information and calculating one or more stability metrics 330. In the example of FIG. 3, the method 300 includes a configurations block 310 that includes intraoperative configurations 312 and chronic configurations 314. The intraoperative configurations 312 pertain to configurations that may be achieved during an operative procedure. For example, during an operative procedure, one or more leads (and/or catheter(s)) may be positioned in a patient where the one or more leads are connected to, or variously connectable to, a device configured to acquire information and optionally to deliver electrical energy to the patient (e.g., to the heart, to a nerve, to other tissue, etc.). The chronic configurations 314 pertain to configurations achievable by a chronically implanted device and its associated lead or leads. In general, intraoperative configurations include those achievable by physically re-positioning a lead (or catheter) in a patient's body while chronic configurations normally do not allow for re-positioning as a lead or leads are usually anchored during implantation or become anchored in the weeks to months after implantation. Chronic configurations do, however, include selection of a subset of the multiple implanted electrodes, for example using the tip electrode versus the first ring electrode as a cathode or using the tip and first ring as a bipolar pair versus using the tip and ring as two independent cathodes. Thus, intraoperative configurations include configurations available by changing device settings, electrode selection, and physical position of electrodes, while chronic configurations include only those configurations available by changing device settings and electrode selection, or "electronic repositioning" of one or more stimulation electrodes.

As indicated in FIG. 3, an acquisition block 320 includes acquisition of position information 322 and optionally acquisition of pacing and/or other information 324 (e.g., electrical information as to electrical activity of the heart, biosensor information, etc.). While an arrow indicates that a relationship or relationships may exist between the configurations block 310 and the acquisition block 320, acquisition of information may occur by using in part an electrode (or other equipment) that is not part of a configuration. For example, the acquisition block 320 may rely on one or more surface electrodes that define a coordinate system or location system for locating an electrode that defines one or more configurations. For example, three pairs of surface electrodes positioned on a patient may be configured to deliver current and define a three-dimensional space whereby measurement of a potential locates an electrode in the three-dimensional space.

As described herein, an electrode may be configured for delivery of energy to the body; for acquisition of electrical information; for acquisition of position information; for acquisition of electrical information and position information; for delivery of energy to the body and for acquisition of electrical information; for delivery of energy to the body and for acquisition of position information; for delivery of energy to the body, for acquisition of electrical information and for acquisition of position information.

In various examples, acquisition of position information occurs by measuring one or more potentials where the measuring relies on an electrode that assists in determining a position of the electrode or other item (e.g., a lead or sensor) where the electrode may also be configured to sense signals and/or deliver energy to the body (e.g., electrical energy to pace a chamber of the heart). For example, an electrode may deliver energy sufficient to stimulate the heart and then be tracked along one or more dimensions to monitor the position information resulting from the stimulation. Further, such an electrode may be used to acquire electrical information (e.g., an IEGM that evidences an evoked response). Such an electrode can perform all three of these tasks with proper circuitry and control. For example, after delivery of the energy, the electrode may be configured for acquiring one or more potentials related to position and for acquiring an electrogram. To acquire potentials and an electrogram, circuitry may include gating or other sampling techniques (e.g., to avoid circuitry or interference issues). Such circuitry may rely on one sampling frequency for acquiring potentials for motion tracking and another sampling frequency for acquiring an electrogram.

The method 300 of FIG. 3 includes a metrics block 330 that includes electrode stability metrics 332, lead stability metrics 334 and implanted device stability metrics 336.

As shown in the example of FIG. 3, the conclusion block 340 may perform actions such as to assess stability 342 and/or to optimize or monitor patient and/or device condition 344. These options are described in more detail with respect to FIG. 4.

Figure 4:
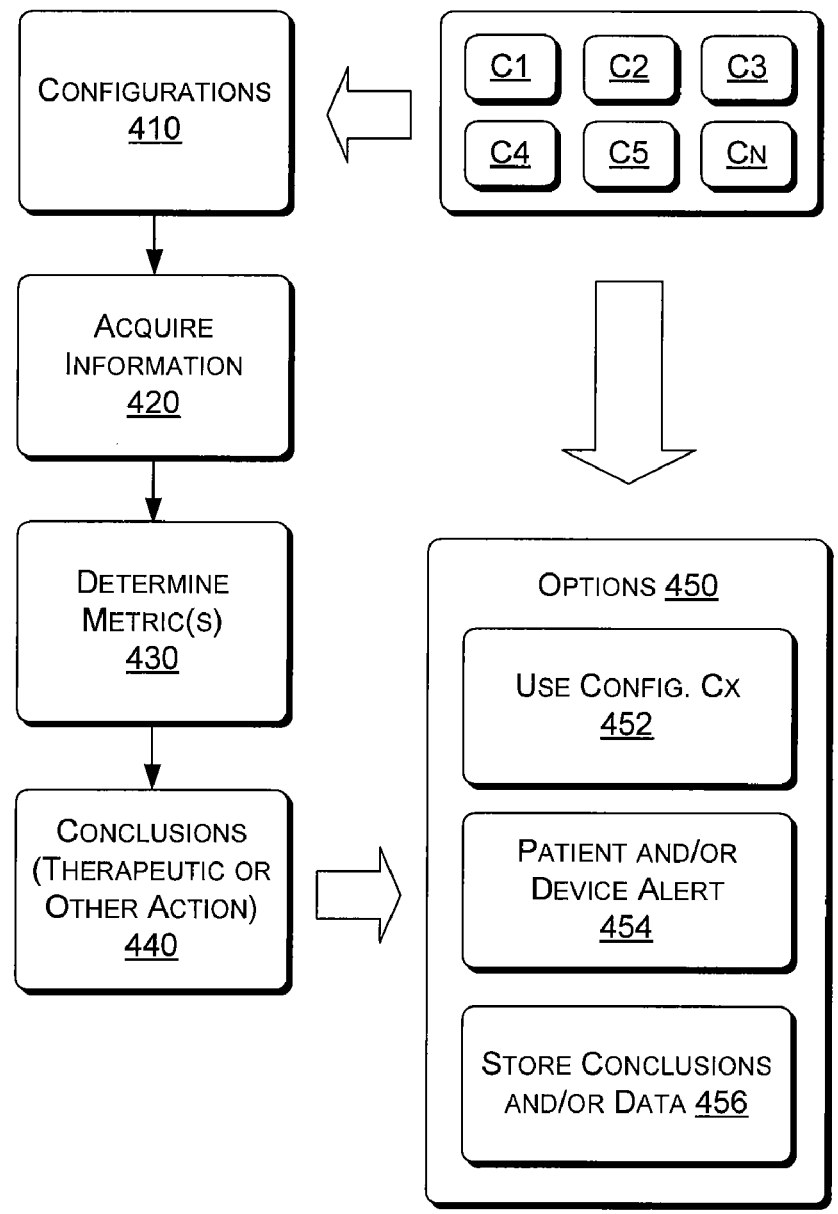
FIG. 4 is a block diagram of the exemplary method of FIG. 3 along with various options.

FIG. 4 shows an exemplary method 400 with various configurations 410 (C1, C2, . . . , Cn) and options 450. As mentioned, a configuration may be defined based on factors such as electrode location (e.g., with respect to some physiological feature of the heart or another electrode), stimulation parameters for an electrode or electrodes and, where appropriate, one or more interelectrode timings. Hence, with reference to FIG. 1, C1 may be a configuration that relies on the RV tip electrode 128, the RV ring electrode 130, the LV tip electrode 122 and the LV ring electrode 124 while C2 may be a configuration that relies on the same electrodes as C1 but where the stimulation polarity for the LV electrodes is reversed. Further, C3 may rely on the same electrodes where the timing between delivery of a stimulus to the RV and delivery of a stimulus to the LV is different compared to C1. Yet further, C4 may rely on the same electrodes where the duration of a stimulus to the RV is different compared to C1. In these foregoing examples, configurations provide for one or more electrodes to deliver energy to stimulate the right ventricle and for one or more electrodes to deliver energy to stimulate the left ventricle. In other examples, configurations may provide for stimulation of a single chamber at one or more sites, stimulation of one chamber at a single site and another chamber at multiple sites, multiple chambers at multiple sites per chamber, etc.

As mentioned, configurations can include one or more so-called "stimulators" and/or "sensors". Thus, the configurations block 410 may select a configuration that includes one or more of an electrode, a lead, a catheter, a device, etc. In various examples, a stimulator or a sensor can include one or more electrodes configured to measure a potential or potentials to thereby directly or indirectly provide position information for the stimulator or the sensor. For example, a lead-based oximeter (oxygen sensor) may include an electrode configured to measure a potential for providing position information for the oximeter or a lead-based RF applicator may include electrodes configured to measure potentials for providing position information for the RF applicator or a tip of the lead.

In an acquisition block 420, acquisition occurs for information where such information includes position information that pertains to one or more electrodes of a configuration. In a determination block 430, one or more stability metrics are determined based at least in part on the acquired information (see, e.g., the metrics block 330 of FIG. 3). A conclusions block 440 provides for therapeutic or other action, which may be selected from one or more options 450.

In the example of FIG. 4, the one or more options 450 include selection of a configuration 452 (e.g., Cx, where x is a number selected from 1 to n), issuance of a patient and/or device alert 454 that pertains to condition of a patient or a condition of a device or associated lead(s) or electrode(s), and storage of conclusion(s) and/or data 456. The options 450 may be associated with the configurations 410, as indicated by an arrow. For example, storage of conclusions and/or data 456 may also store specific configurations, a generalization of the configurations (e.g., one or more shared characteristics), a device/system arrangement (e.g., where the number and types of configurations would be known based on the arrangement), etc. With respect to an alert per block 454, an exemplary method may determine a stability limit as an indicator of instability or risk of instability. Such a limit may be a metric or index, for example, based on impedance of a known unstable configuration (e.g., a standard deviation of impedance measurements) as acquired in an acute setting. Accordingly, where impedance measured in a chronic setting exhibits a metric or index that exceeds the limit, an alert may be issued.

As described herein, an exemplary method can include: locating one or more electrodes within the heart and/or surrounding space (e.g., intra-chamber, intra-vascular, intraperi-cardial, etc., which may be collectively referred to as "cardiac space"); and acquiring information (e.g., via one or more measured potentials) to calculate one or more stability metrics for at least one of the one or more electrodes using an electroanatomic mapping system (e.g., the ENSITE® NAVX® system or other system with appropriate features). In such a method, the located electrodes may be configured for acquisition of electrical information indicative of physiological function (e.g., IEGMs, muscle signals, nerve signals, etc.). Further, with respect to acquisition of information, an acquisition system may operate at an appropriate sampling rate. For example, an acquisition system for position information may operate at a sampling rate of about 100 Hz (e.g., the ENSITE® NAVX® system can sample at about 93 Hz) and an acquisition system for electrical information may operate at a sampling rate of about 1200 Hz (e.g., in unipolar, bipolar or other polar arrangement).

An exemplary method may include preparing a patient for both implant of a device such as the device 100 of FIGS. 1 and 2 and for electroanatomic mapping study. Such preparation may occur in a relatively standard manner for implant prep, and using the ENSITE® NAVX® system or other similar technology for the mapping prep. As described herein, any of a variety of electroanatomic mapping or locating systems that can locate indwelling electrodes in and around the heart may be used.

Once prepped, a clinician or robot may place leads and/or catheters in the patient's body, including any leads to be chronically implanted as part of a therapy system (e.g., CRT), as well as optional additional electrodes that may yield additional information (e.g., to increase accuracy by providing global information or other information).

After an initial placement of an electrode-bearing catheter or an electrode-bearing lead, a clinician may then connect one or more electrodes to an electroanatomic mapping or localizing system. The term "connection" can refer to physical electrical connection or wireless connection (e.g., telemetric, RF, ultrasound, etc.) with the electrodes or wireless connection with another device that is in electrical contact with the electrodes.

Once an appropriate connection or connections have been made, real-time position data for one or more electrodes may be acquired for various configurations or conditions. For example, position data may be acquired during normal sinus rhythm; pacing in one or more chambers; advancing, withdrawing, or moving a location of an electrode; pacing one or more different electrode configurations (e.g. multisite pacing); or varying inter-stimulus timing (e.g. AV delay, VV delay).

In various examples, simultaneous to the position recording, an intracardiac electrogram (IEGM) from each electrode can also be recorded and associated with the anatomic position of the electrode. While various examples refer to simultaneous acquisition, acquisition of electrical information and acquisition of position information may occur sequentially (e.g., alternate cardiac cycles) or interleaved (e.g., both acquired during the same cardiac cycle but offset by sampling time or sampling frequency).

In various exemplary methods, electrodes within the cardiac space may be optionally positioned at various locations (e.g., by continuous movement or by discrete, sequential moves), with a mapping system recording the real-time position information at each electrode position in a point-by-point manner. Such position data can by associated with a respective anatomic point from which it was collected. By moving the electrodes from point to point during an intervention, the position data from each location can be incorporated into a single map, model, or parameter.

As explained, an exemplary method may include mapping one or more stability metrics and/or parameters. In turn, an algorithm or a clinician may select a configuration (e.g., electrode location, multisite arrangement, AV/VV timing) that yielded the best value for an electromechanical delay parameter and use the selected configuration as a chronic configuration for the CRT system. Such a chronic configuration may be optionally updated from time to time (e.g., during a follow-up visit, in a patient environment, etc., depending on specific capabilities of a system).

Various exemplary methods, using either a single metric or a combination of more than one metric, may automatically select a configuration, present an optimal configuration for acknowledgement by a clinician, or present various configurations to a clinician along with pros and cons of each configuration (e.g., in objective or subjective terms). For example, a particular configuration may be associated with a high power usage that may excessively drain a power source of an implantable device (e.g., device battery 276). Other pros and cons may pertain to patient comfort (e.g., pain, lack of pain, overall feeling, etc.). As described herein, various decisions are based on stability of one or more of an electrode or a lead.

An exemplary method may rely on certain equipment at time of implant or exploration and other equipment after implantation of a device to deliver a cardiac therapy. For example, during an intraoperative procedure, wireless communication may not be required; whereas, during a follow-up visit, measured potentials for position of chronically implanted electrodes (e.g., mechanical information) and of measured IEGMs using chronically implanted electrodes (e.g., electrical information) may be communicated wirelessly from an implanted device to an external device. With respect to optimization or assessment of a chronically implanted system, in general, electrode location will not be altered (e.g., except for dislocation or failure), but other parameters altered to result in an optimal configuration (e.g., single- or multi-site arrangement, polarity, stimulation energy, timing parameters, etc.).

As discussed herein, various exemplary techniques deliver current and measure potential where potential varies typically with respect to cardiac mechanics (e.g., due to motion). For example, electrodes for delivery of current may be placed at locations that do not vary significantly with respect to cardiac mechanics or other patient motion (e.g., breathing) while one or more electrodes for measuring potential may be placed at a location or locations that vary with respect to cardiac mechanics or other patient motion. Alternatively, electrodes for measuring potential may be placed at locations that do not vary significantly with respect to cardiac mechanics or other patient motion while one or more electrodes for delivery of current may be placed at a location or locations that vary with respect to cardiac mechanics or other patient motion. Various combinations of the foregoing arrangements are possible as well. Electrodes may be associated with a catheter or a lead. In some instances, an electrode may be a "stand-alone" electrode, such as a case electrode of an implantable device (see, e.g., the case electrode 200 of the device 100 of FIGS. 1 and 2).

Figure 5:
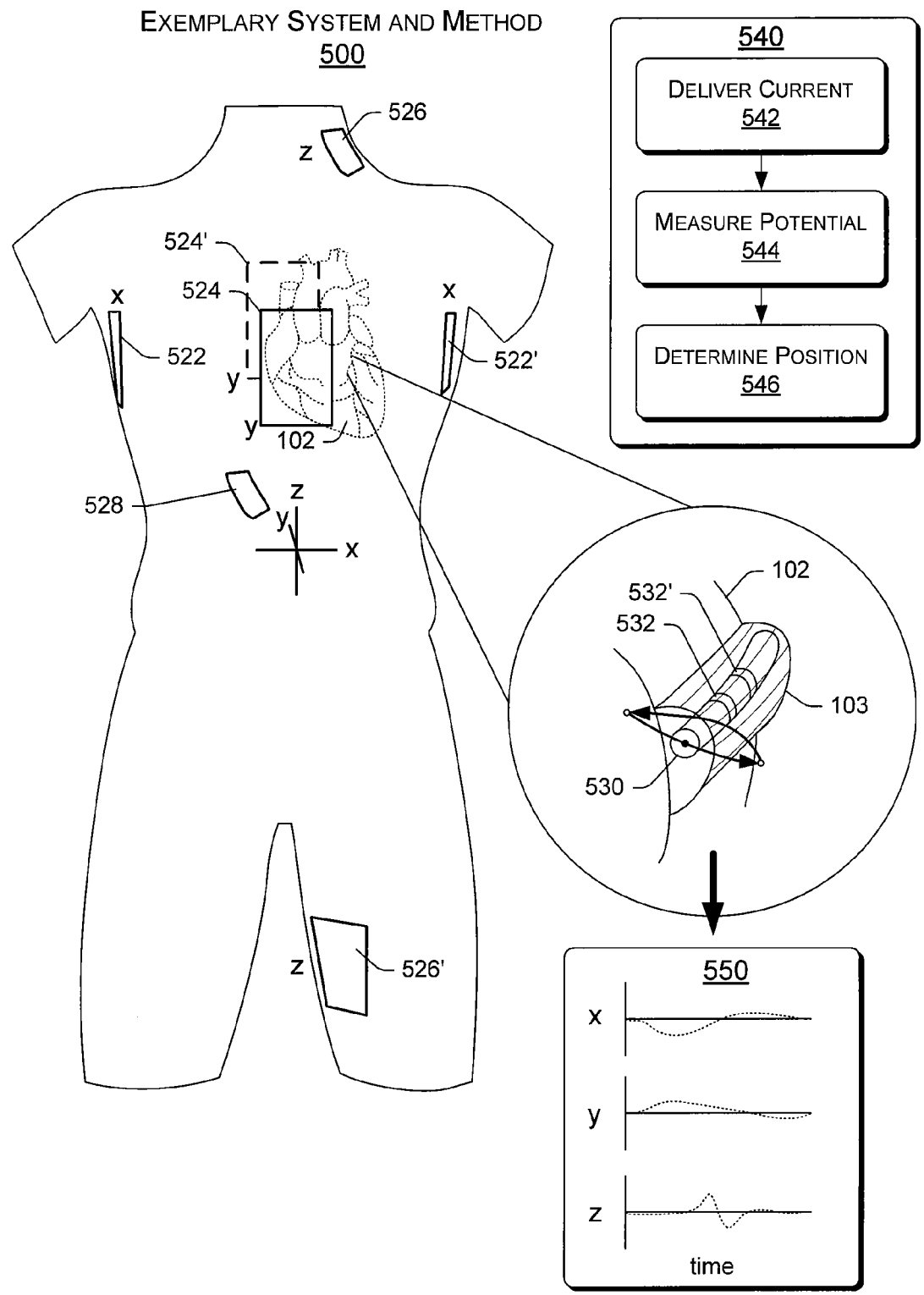
FIG. 5 is an exemplary arrangement of a lead and electrodes for acquiring position information and optionally other information for use in determining one or more stability metrics.

FIG. 5 shows an arrangement and method 500 that may rely in part on a commercially available system marketed as ENSITE® NAVX® navigation and visualization system (see also LocaLisa system). The ENSITE® NAVX® system is a computerized storage and display system for use in electrophysiology studies of the human heart. The system consists of a console workstation, patient interface unit, and an electrophysiology mapping catheter and/or surface electrode kit. By visualizing the global activation pattern seen on color-coded isopotential maps in the system, in conjunction with the reconstructed electrograms, an electrophysiologist can identify the source of an arrhythmia and can navigate to a defined area for therapy. The ENSITE® system is also useful in treating patients with simpler arrhythmias by providing non-fluoroscopic navigation and visualization of conventional electrophysiology (EP) catheters.

As shown in FIG. 5, electrodes 532, 532', which may be part of a standard EP catheter 530 (or lead), sense electrical potential associated with current signals transmitted between three pairs of surface electrode patches 522, 522' (x-axis), 524, 524' (y-axis) and 526, 526' (z-axis). An addition electrode patch 528 is available for reference, grounding or other function. The ENSITE® NAVX® System can also collect electrical data from a catheter and can plot a cardiac electrogram from a particular location (e.g., cardiac vein 103 of heart 102). Information acquired may be displayed as a 3-D isopotential map and as virtual electrograms. Repositioning of the catheter allows for plotting of cardiac electrograms from other locations. Multiple catheters may be used as well. A cardiac electrogram or electrocardiogram (ECG) of normal heart activity (e.g., polarization, depolarization, etc.) typically shows atrial depolarization as a "P wave", ventricular depolarization as an "R wave", or QRS complex, and repolarization as a "T wave". The ENSITE® NAVX® system may use electrical information to track or navigate movement and construct three-dimensional (3-D) models of a chamber of the heart.

A clinician can use the ENSITE® NAVX® system to create a 3-D model of a chamber in the heart for purposes of treating arrhythmia (e.g., treatment via tissue ablation). To create the 3-D model, the clinician applies surface patches to the body. The ENSITE® NAVX® system transmits an electrical signal between the patches and the system then senses the electrical signal using one or more catheters positioned in the body. The clinician may sweep a catheter with electrodes across a chamber of the heart to outline structure. Signals acquired during the sweep, associated with various positions, can then be used to generate a 3-D model. A display can display a diagram of heart morphology, which, in turn, may help guide an ablation catheter to a point for tissue ablation.

With respect to the foregoing discussion of current delivery and potential measurement, per a method 540, a system (e.g., such as the ENSITE® NAVX® system) delivers low level separable currents from the three substantially orthogonal electrode pairs (522, 522', 524, 524', 526, 526') positioned on the body surface (delivery block 542). The specific position of a catheter (or lead) electrode within a chamber of the heart can then be established based on three resulting potentials measured between the recording electrode with respect to a reference electrode, as seen over the distance from each patch set to the recording tip electrode (measurement block 544). Sequential positioning of a catheter (or lead) at multiple sites along the endocardial surface of a specific chamber can establish that chamber's geometry, i.e., position mapping (position/motion determination block 546). Where the catheter (or lead) 530 moves, the method 540 may also measure motion.

In addition to mapping at specific points, the ENSITE® NAVX® system provides for interpolation (mapping a smooth surface) onto which activation voltages and times can be registered. Around 50 points are required to establish a surface geometry and activation of a chamber at an appropriate resolution. The ENSITE® NAVX® system also permits the simultaneous display of multiple catheter electrode sites, and also reflects real-time motion of both ablation catheters and those positioned elsewhere in the heart.

The ENSITE® NAVX® system relies on catheters for temporary placement in the body. Various exemplary techniques described herein optionally use one or more electrodes for chronic implantation. Such electrodes may be associated with a lead, an implantable device, or other chronically implantable component. Referring again to FIG. 3, the configuration block 310 indicates that intraoperative configurations 312 and chronic configurations 314 may be available. Intraoperative configurations 312 may rely on a catheter and/or a lead suitable for chronic implantation.

With respect to motion (e.g., change in position with respect to time), the exemplary system and method 500 may track motion of an electrode in one or more dimensions. For example, a plot 550 of motion versus time for three dimensions corresponds to motion of one or more electrodes of the catheter (or lead) 530 positioned in a vessel 103 of the heart 102 where the catheter (or lead) 530 includes the one or more electrodes 532, 532'. Two arrows indicate possible motion of the catheter (or lead) 530 where hysteresis may occur over a cardiac cycle. For example, a systolic path may differ from a diastolic path. An exemplary method may analyze hysteresis for any of a variety of purposes including assessing stability of an electrode of a catheter (or lead), assessing stability of a catheter (or lead), selection of a stimulation site, selection of a sensing site, diagnosis of cardiac condition, etc.

The exemplary method 540, as mentioned, includes the delivery block 542 for delivery of current, the measurement block 544 to measure potential in a field defined by the delivered current and the determination block 546 to determine position or motion based at least in part on the measured potential. According to such a method, position or motion during systole and/or diastole may be associated with electrical information or other information (e.g., biosensor, loading of a catheter or lead, intrinsic/paced activation, etc.). Alone, or in combination with other information, the position or motion information may be used for various assessments (e.g., stability assessments), selection of optimal stimulation site(s), determination of hemodynamic surrogates (e.g., surrogates to stroke volume, contractility, etc.), optimization of CRT, placement of leads, determination of pacing parameters (AV delay, VV delay, etc.), etc.

The system 500 may use one or more features of the aforementioned ENSITE® NAVX® system. For example, one or more pairs of electrodes (522, 522', 524, 524', 526, 526' and optionally 528) may be used to define one or more dimensions by delivering an electrical signal or signals to a body and/or by sensing an electrical signal or signals. Such electrodes (e.g., patch electrodes) may be used in conjunction with one or more electrodes positioned in the body (e.g., the electrodes 532, 532').

The exemplary system 500 may be used to track position or motion of one or more electrodes due to systolic function, diastolic function, respiratory function, etc. Electrodes may be positioned along the endocardium and/or epicardium during a scouting or mapping process for use in conjunction with electrical information. Such information may also be used alone, or in conjunction with other information (e.g., electrical information), for assessing stability of an electrode or electrodes for use in delivering a therapy or for identifying the optimal location of an electrode or electrodes for use in delivering a therapy. For example, a location may be selected for optimal stability, for optimal stimulation, for optimal sensing, or for other purposes.

With respect to stimulation, stimulation may be delivered to control cardiac mechanics (e.g., contraction of a chamber of the heart) and position or motion information may be acquired where such information is associated with the controlled cardiac mechanics. An exemplary selection process may identify the best stimulation site based on factors such as electrical activity, electromechanical delay, extent of motion, synchronicity of motion where motion may be classified as motion due to systolic function or motion due to diastolic function. In general, motion information corresponds to motion of an electrode or electrodes (e.g., endocardial electrodes, epicardial electrodes, etc.) and may be related to motion of the heart or other physiology.

As described with respect to FIG. 5, a localization system can acquire position information for one or more electrodes on a lead or catheter. The ENSITE® NAVX® system can operate at a sampling frequency around 100 Hz (10 ms), which, for a cardiac rhythm of 60 bpm, allows for 100 samples per electrode per cardiac cycle. In various examples, sampling may be gated to occur over only a portion of a cardiac cycle. Gating may rely on fiducial markers such as peaks, gradients, crossings, etc., in an electrogram of heart activity. Other techniques for gating can include accelerometer techniques, impedance techniques, pressure techniques, flow techniques, etc. For example, an accelerometer signal slope above a threshold value (e.g., due to cardiac contraction or relaxation) can be used to commence acquisition of information or to terminate acquisition of information during a cardiac cycle. Such a technique may be repeated over multiple cardiac cycles with or without application of electrical stimuli, medication, body position changes, etc.

As described herein, for one or more electrodes, a localization system provides four-dimensional information (e.g., x, y, z and time). The four-dimensional information describes a three-dimensional trajectory in space that can be analyzed or displayed in part, in whole or at one or more key points in time. As mentioned, various other types of information may be used to gate acquisition or to delineate points or segments of a trajectory. For example, information provided by a surface EKG, an intracardiac EGM, or other biosignal can delineate a point or event such as QRS onset or pacing pulse or a segment (e.g., QRS complex, QT interval, etc.).

Where an electrode is position in a vessel of the heart such as a vein (e.g., cardiac sinus (CS) vein or a tributary thereto), the trajectory of the electrode will follow cardiac motion of nearby myocardium. For example, a CS lead electrode will trace the path traversed by epicardium adjacent the CS or adjacent the particular CS tributary. If the lead position is stable in a branch, the trajectory for consecutive beats will typically remain within a bounded spatial volume; however, if the lead dislodges grossly, a shift in the CS lead electrode's position will be apparent in a display or analysis of the acquired information.

Figure 6:
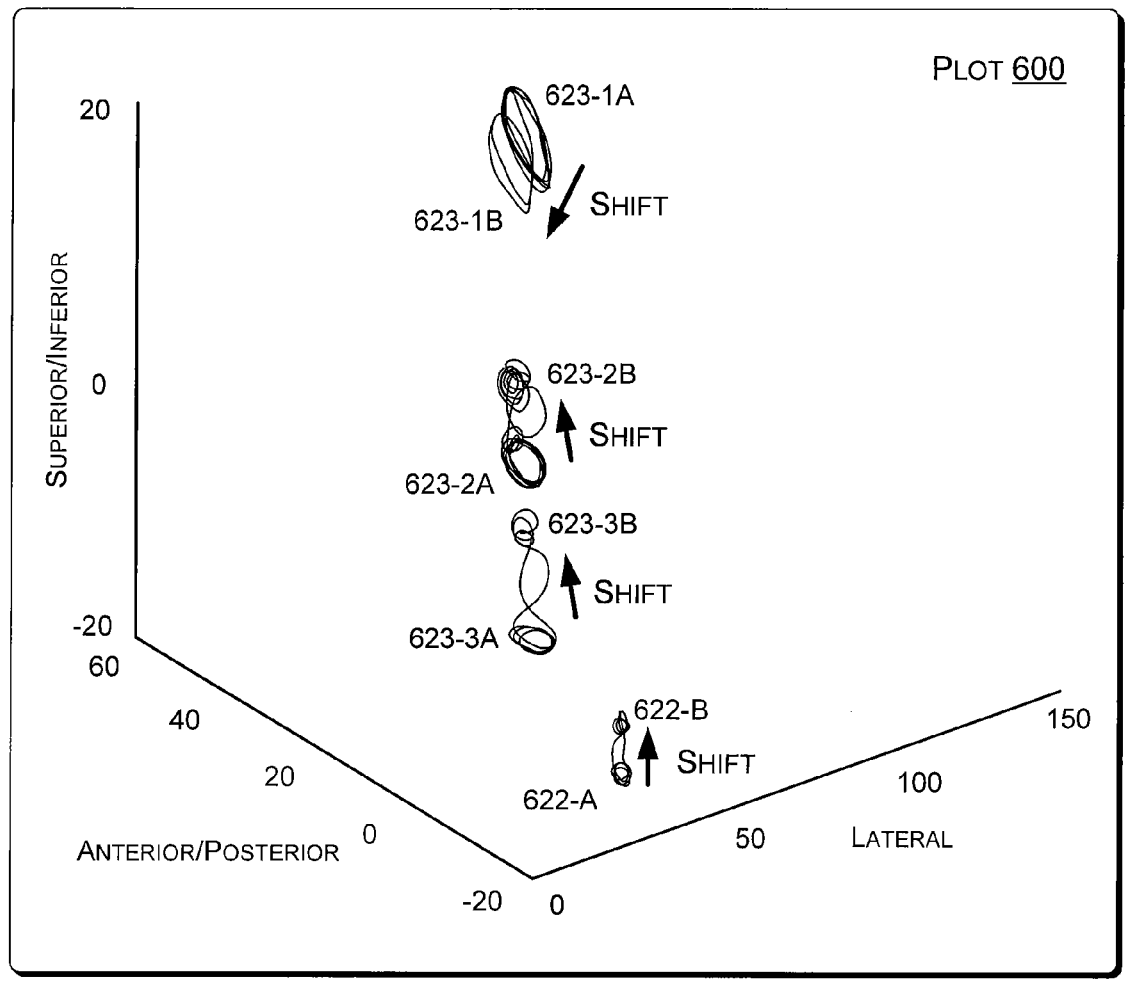
FIG. 6 is a plot of position information with respect to time for a series of electrodes of a lead where a shift has occurred as evidenced by relatively distinct groupings of electrode position traces or trajectories in a three-dimensional space.

FIG. 6 shows a plot 600 of trajectories based on position information acquired for four electrodes 623-1, 623-2, 623-3 and 622 of a quadpolar LV lead in a CS branch of a canine model over a number of cardiac cycles. Each of the trajectories can be characterized as defining a first cluster ("A") and a second cluster ("B"). In the example of FIG. 6, for the electrode 623-1, the direction of the shift from cluster A to cluster B differs from that of the other electrodes 623-2, 623-3 and 622. An analysis of shift direction for a lead (e.g., on an electrode-by-electrode basis) can indicate mechanisms underlying a shift. For example, if slack exists in a lead between two adjacent electrodes, a shift may reduce the slack where the two adjacent electrodes move in substantially opposite directions. Another mechanism is dislodgement, which may occur for any of a variety of reasons including body or organ movements caused by coughing, phrenic nerve stimulation or delivery of a defibrillation shock. Dislodgement may also occur where a lead or electrode anchor fails. Further, a shift may occur upon withdrawal of a stylet (e.g., consider a lead body that has greater flexibility after withdrawal of a stylet).

Figure 7:
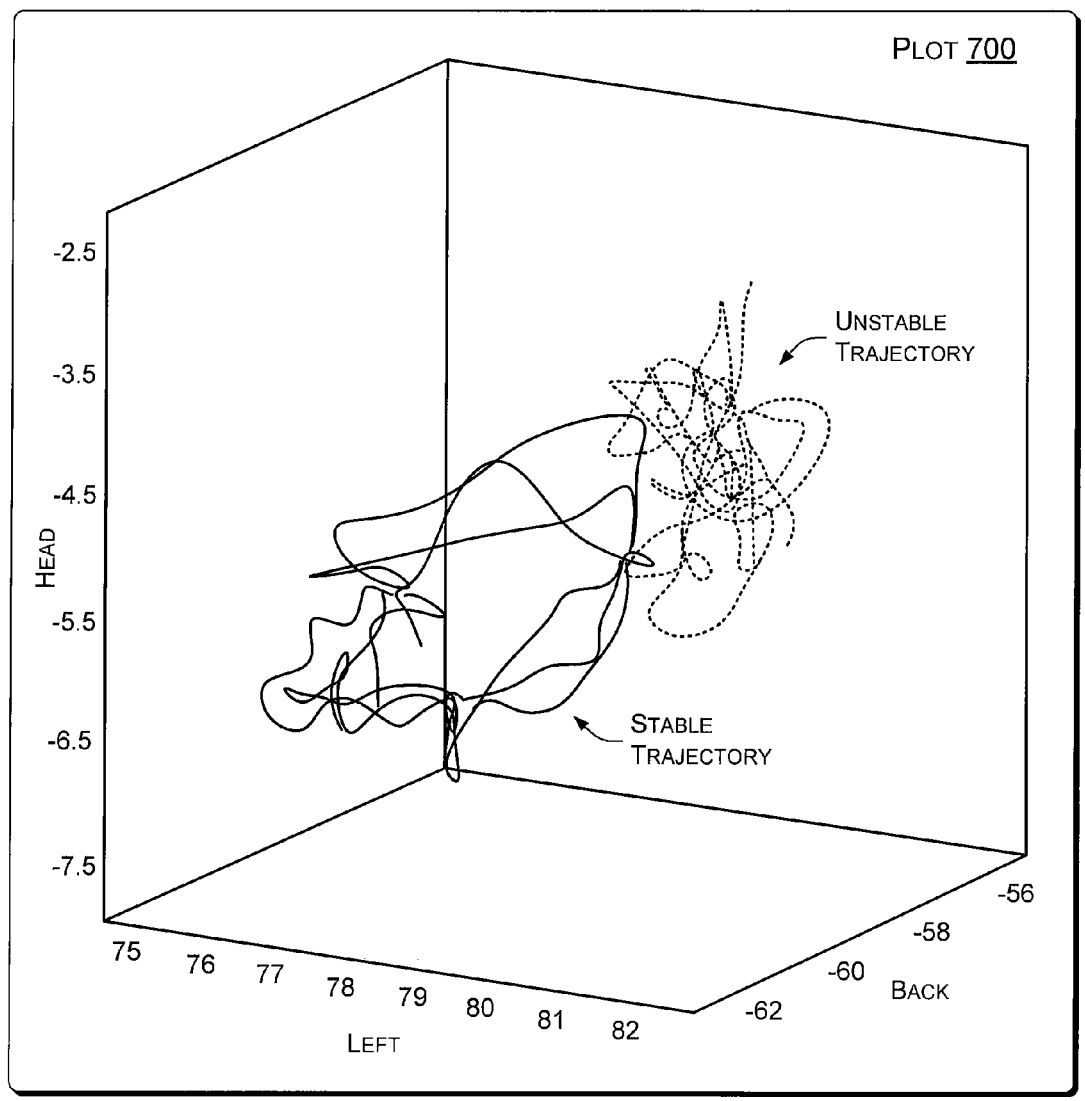
FIG. 7 is a plot of position information with respect to time over multiple cardiac cycles for two electrode locations where in one location the electrode exhibits a relatively stable trajectory and where the other location the electrode exhibits a less stable or unstable trajectory.

FIG. 7 shows a plot 700 of a stable trajectory and an unstable trajectory based on position information acquired for a cardiac lead of a patient. Lead electrodes in good stable contact with the epicardium or endocardium tend to trace similar trajectories for every cardiac cycle (e.g., especially for a consistent beat). To the contrary, lead electrodes in poor contact with the epicardium or endocardium (e.g., if a CS lead is not securely wedged in a branch), tend to bounce around erratically from beat to beat, even when general position of the lead appears stable.

As described herein, various exemplary methods acquire and analyze position information to indicate whether an electrode is stable. Stability criteria may be applied to analyzed information acquired during an intraoperative procedure (e.g., acute state) to increase the probability that an electrode will be stable after the intraoperative procedure (e.g., chronic state).

After implant, the body responds to the foreign electrode. The response can be similar to a wound healing process characterized by inflammation and collagen formation (e.g., fibrous encapsulation). The body's response to an implanted electrode can be tracked to some extent by measuring capture threshold for an electrode configuration that uses the electrode or by measuring impedance of a circuit that includes the electrode. Often, the capture threshold rises over the first few days following implant and then declines to a relatively constant value over a period of weeks (e.g., six to ten weeks). As the capture threshold depends on contact between the electrode and the body, stability of the electrode-myocardial interface may also be understood via capture threshold and impedance measurements. Factors such as electrode location, size, shape, chemical composition and surface structure can affect how the body responds post-implant.

Given sufficient data for specific or general electrode types, stability criteria can be determined and applied to data acquired in an acute state. For example, an electrode known to have few stability issues post-implant may have stability criteria that allow for larger trajectories or more erratic trajectories whereas an electrode known to have more stability issues post-implant may have stability criteria that dictate small trajectories with small standard deviation. Further, stability criteria may be applied regionally and optionally with respect to electrode function. For example, an electrode to be used for sensing may have a greater tolerance to instability while an electrode to be used for pacing may have a lesser tolerance to instability. Thus, as described herein, stability criteria may depend on any of a variety of factors.

Figure 8:
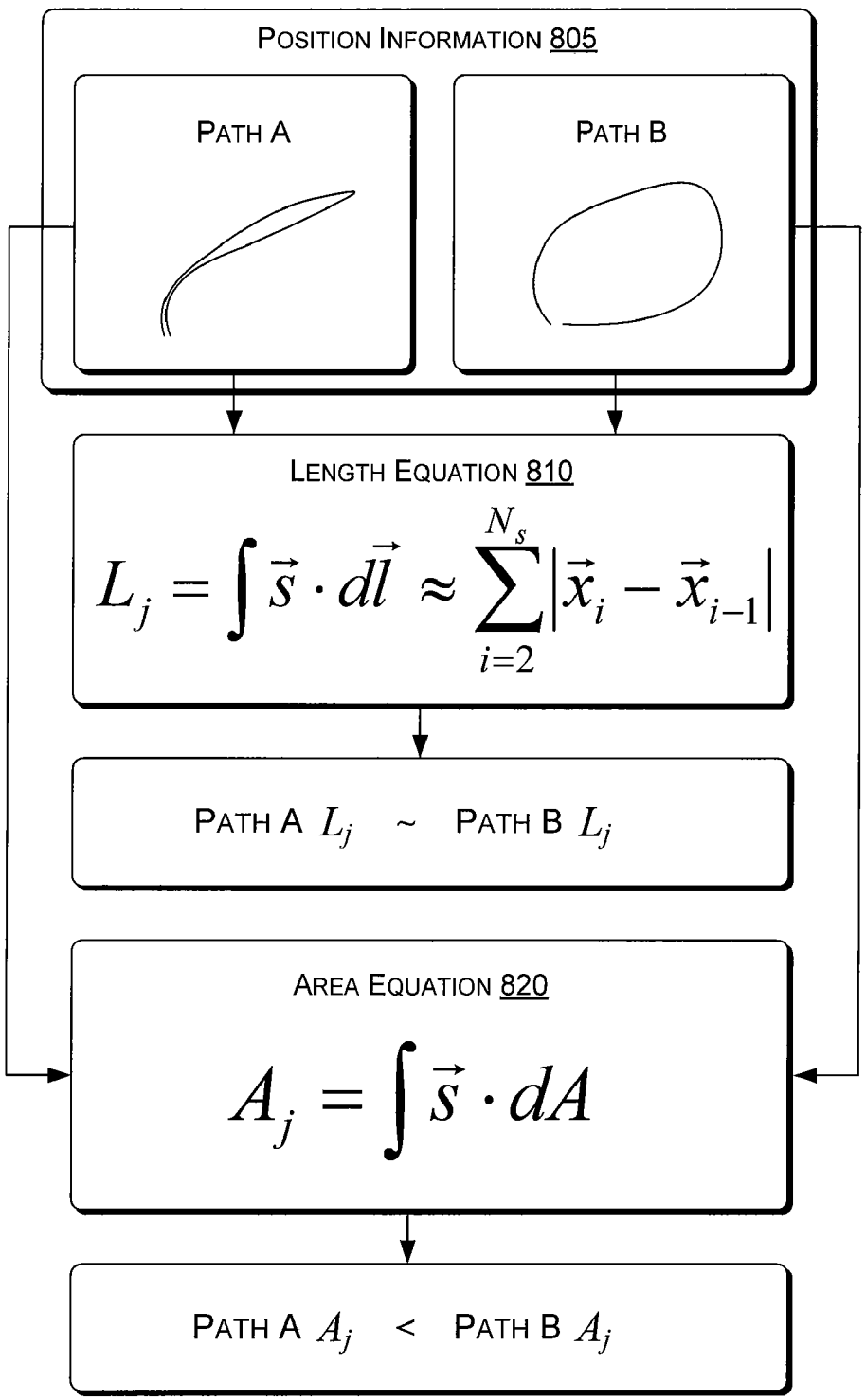
FIG. 8 is a block diagram of an exemplary method for determining a path length metric and a path area metric and for comparing such metrics for different paths.

To assess stability of an electrode, an exemplary method may determine one or more exemplary metrics. FIG. 8 shows an exemplary method 800 along with position information 805, a length equation 810 and an area equation 820 that may be used to determine a length metric "$L_j$" and an area metric "$A_j$", respectively. To illustrate how these two metrics may be used alone or in combination, position information 805 is shown for two paths: Path A and Path B. For the $j^{th}$ cardiac cycle, sampled at $N_s$ time points, the path length $L_j$ can be determined based on the length equation 810, i.e., by the integral of an electrode position vector $\vec{s}$ over a trajectory length (dl) or by its discrete approximation of position $\vec{x}$ over the number of sampled time points $N_s$. Given Path A and Path B, which are shown in respective planes that correspond to maximum area, length metrics per the length equation 810 indicate that the length of Path A is approximately the same as the length of Path B. To distinguish characteristics of Path A from Path B, the area equation 820 may be used. The area equation 820 is given in FIG. 8 as an integral of the electrode position vector $\vec{s}$ over an area (dA) (e.g., consider the planes as shown for Path A and Path B). In various instances, area enclosed by a swept path can be used as a single cycle indicator as an electrode normally returns to approximately the same point. In the example of FIG. 8, the area metrics per the area equation 820 indicate that Path B sweeps a larger area than Path A. As described herein, path metrics such as path length and path area can indicate whether an electrode is in a stable location or an unstable location (e.g., based on one or more stability criteria). Further, such metrics can help determine an optimal electrode location that accounts for stability and desired therapeutic function (e.g., sensing, pacing, shocking, etc.).

FIG. 9 shows an exemplary method 900 that computes various stability index metrics. Specifically, given position information 905, the method 900 can compute a stability index sum metric, a stability index mean metric and a stability index standard deviation metric, for example, per a $SI_{sum}$ equation 910, a $SI_{mean}$ equation 920 and a $SI_{stddev}$ equation 930, respectively. In the equations 910 and 920, an index j represents a number of cardiac cycles from 1 to $N_c$ while an index i represents a number of time fiducials from 1 to $N_f$. The position information 905 is shown with labels that indicate a number of cardiac cycles from 1 to $N_c$ and a number of time fiducials from 1 to $N_f$. In the equations 910 and 920, the vector $\vec{x}$ represents a particular position of an electrode in a three-dimensional space for a given cardiac cycle and for a time fiducial within the given cardiac cycle.

As described herein, for a lead of which stability is desired to be known, position information is acquired at one or more gated points in a cardiac cycle. In a particular implementation, position of an electrode at a single fiducial time point is the only required information; in another implementation, position of an electrode is traced as a complete trajectory for all samples (e.g., for multiple fiducial time points). Over the course of two or more cardiac cycles (e.g., consecutive, alternate, etc.), electrode position at each corresponding gated point is noted.

With respect to stability metrics, an exemplary method may compute distance in three dimensions between positions at like time points of different cardiac cycles. In implementations that utilize a single or a small number of time points, the distance between like time points, or the sum or average of distances between multiple like time points, is an index of stability, such that the smaller the distance or sum or average of distances, the more stable the position. The equation 910 can be used to determine such a sum where a reference cardiac cycle may be selected for calculating distance between a position for a fiducial point in the reference cardiac cycle and a position for the same fiducial point in another cardiac cycle. The equation 920 can be used to determine a stability index mean in a similar manner.

With respect to standard deviation, such a statistical measure may be applied to various forms of position information. Per the equation 930, a standard deviation stability index can be determined for a length $L_j$. In this example, the standard deviation corresponds to changes in path length of an electrode over multiple cardiac cycles. Similarly, standard deviation may be determined for a swept area, a cycle-to-cycle distance at a time fiducial (e.g., given a reference position), etc.

As mentioned, differing pacing interventions as well as external forces on an electrode-bearing lead can affect stability in a given location. A stability index can be calculated from the electrode(s) motion stability during intrinsic and paced rhythm or with zero mechanical loading and some mechanical loading to the lead by pulling a proximal portion of the lead. For example, predictors of lead dislodgement can be derived as follows: $(SI_{intrinsic} - SI_{paced})/SI_{intrinsic}$ or $(SI_{no\ load} - SI_{loaded})/SI_{no\ load}$.

Figure 10:
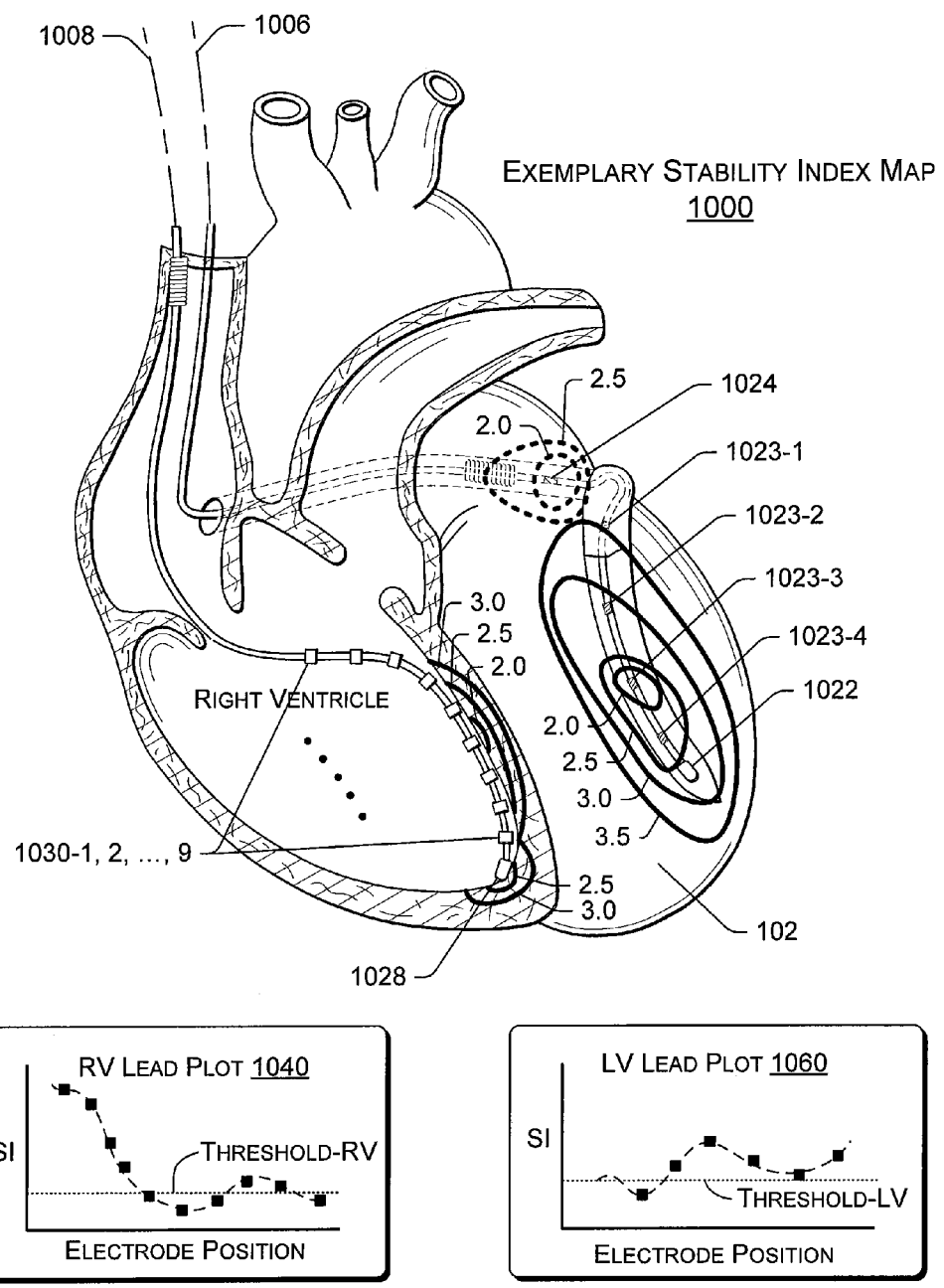
FIG. 10 is a diagram of an exemplary stability metric map and associated plots of stability index versus electrode position or number for electrodes of a right ventricular lead and for electrodes of a left ventricular lead (e.g., a coronary sinus lead).

As described herein, various stability metrics may be mapped with respect to one or more anatomical markers. FIG. 10 shows an exemplary stability index map 1000 where contours indicate stability metric values at various regions of the heart 102. In cases where a clinician desires to map various CS lead locations in order to find an acceptable location, the inclusion of a point-wise stability indicator on a map is possible. For example, at each candidate location, position information may be acquired for two or more cardiac cycles. Such information may be analyzed to provide one or more stability metrics (e.g., consider a local stability index). As each candidate location is probed for stability, a patch of color can be displayed on an anatomic map showing, for example, relative stability at that location. Such a map can be overlaid with other electroanatomic or physio-anatomic map data such as voltage map data, activation time map data, hemodynamic response map data, etc.

ventricle or specific to the left ventricle. Such a threshold may assist a clinician in site selection for an electrode or in programming an implantable device for sensing cardiac electrical activity and/or delivering electrical energy to the heart 102. For example, where an implantable device relies on accurate IEGM data to adjust a pacing parameter, a criterion may exist that prohibits use of an electrode having a stability index below a threshold value. Thus, given the plot 1040, a clinician may program an implantable device to prohibit use of the electrodes 1030-5, 6, 7 and 1028 from sensing for the particular purpose of adjusting the pacing parameter. In this example, the values of the thresholds may be based on historic stability data or physiological models that may indicate signal-to-noise ratio or other criteria germane to sensing (e.g., if stability is less than Y, then SNR will exceed Z).

Referring again to the map 1000 of FIG. 10, a left ventricular lead 1006 is shown as including various electrodes 1022, 1023-1 to 1023-4, and 1024 located in the coronary sinus or a tributary vein of the coronary sinus (e.g., along a lateral wall of the left ventricle) and a right ventricular lead 1008 is shown as including various electrodes 1028, 1030-1 to 1030-9, some of which contact the septal wall between the right ventricle and the left ventricle. The contours indicate stability index values, which may be dimensionless and normalized such that a higher number corresponds to increased stability.

FIG. 10 also shows a plot 1040 of stability index versus electrode position (or electrode order) on the RV lead 1008 and a plot 1060 of stability index versus electrode position (or electrode order) on the LV lead 1006. In each of the plots 1040 and 1060, a threshold value is shown, which, in this example, is specific to the right ventricle or specific to the left ventricle. Such a threshold may assist a clinician in site selection for an electrode or in programming an implantable device for sensing cardiac electrical activity and/or delivering electrical energy to the heart 102. For example, where an implantable device relies on accurate IEGM data to adjust a pacing parameter, a criterion may exist that prohibits use of an electrode having a stability index below a threshold value. Thus, given the plot 1040, a clinician may program an implantable device to prohibit use of the electrodes 1030-5, 6, 7 and [[9]] 1028 from sensing for the particular purpose of adjusting the pacing parameter. In this example, the values of the thresholds may be based on historic stability data or physiological models that may indicate signal-to-noise ratio or other criteria germane to sensing (e.g., if stability is less than Y, then SNR will exceed Z).

FIG. 11 shows an exemplary method 1100 with two sub-methods, one method 1104 for acquiring position information during intrinsic activation of the heart and another method 1108 for acquiring position information during paced activation of the heart. Further, as indicated in FIG. 11, information acquired from the method 1104 and the method 1108 may be relied up in a hybrid method 1106.

The method 1104 commences in a configuration selection block 1110, which is followed by an information acquisition block 1114. After or during acquisition, an analysis block 1118 analyzes the position information and a conclusion block 1122 makes one or more conclusions based on the analysis. The method 1108 operates in a similar manner to the method 1104 but includes pacing. As shown in FIG. 11, the method 1108 commences in a configuration selection block 1130, which is followed by an implementation block 1132 that implements pacing. An information acquisition block 1134 follows where, after or during acquisition, an analysis block 1138 analyzes the position information and a conclusion block 1142 makes one or more conclusions based on the analysis.

As described herein, the methods 1104 and 1108 may be performed successively or alternately (e.g., perform method 1104 for three minutes, perform method 1108 for two minutes, etc.). As mentioned, the hybrid method 1106 may include acquiring information from the acquisition blocks 1114 and 1134 and analyzing such acquired information in an analysis block 1150 where the analyzed information can be relied on to make one or more conclusions per a conclusions block 1154.

According to the hybrid method 1106, with respect to the analysis block 1150, a linear dislodgement intrinsic/paced index may be calculated and with respect to the conclusions block 1154, conclusions may be instability for a configuration with intrinsic activation and increased stability for the configuration with paced activation. In another instance, an area dislodgement intrinsic/paced index may be calculated and conclusions made that a small trajectory exists for a configuration with intrinsic activation and a larger trajectory exists for the configuration with paced activation. Such conclusions may indicate that pacing can alter the stability of the configuration, for example, possibly creating an environment that is likely to decrease stability of the configuration.

Figure 12:
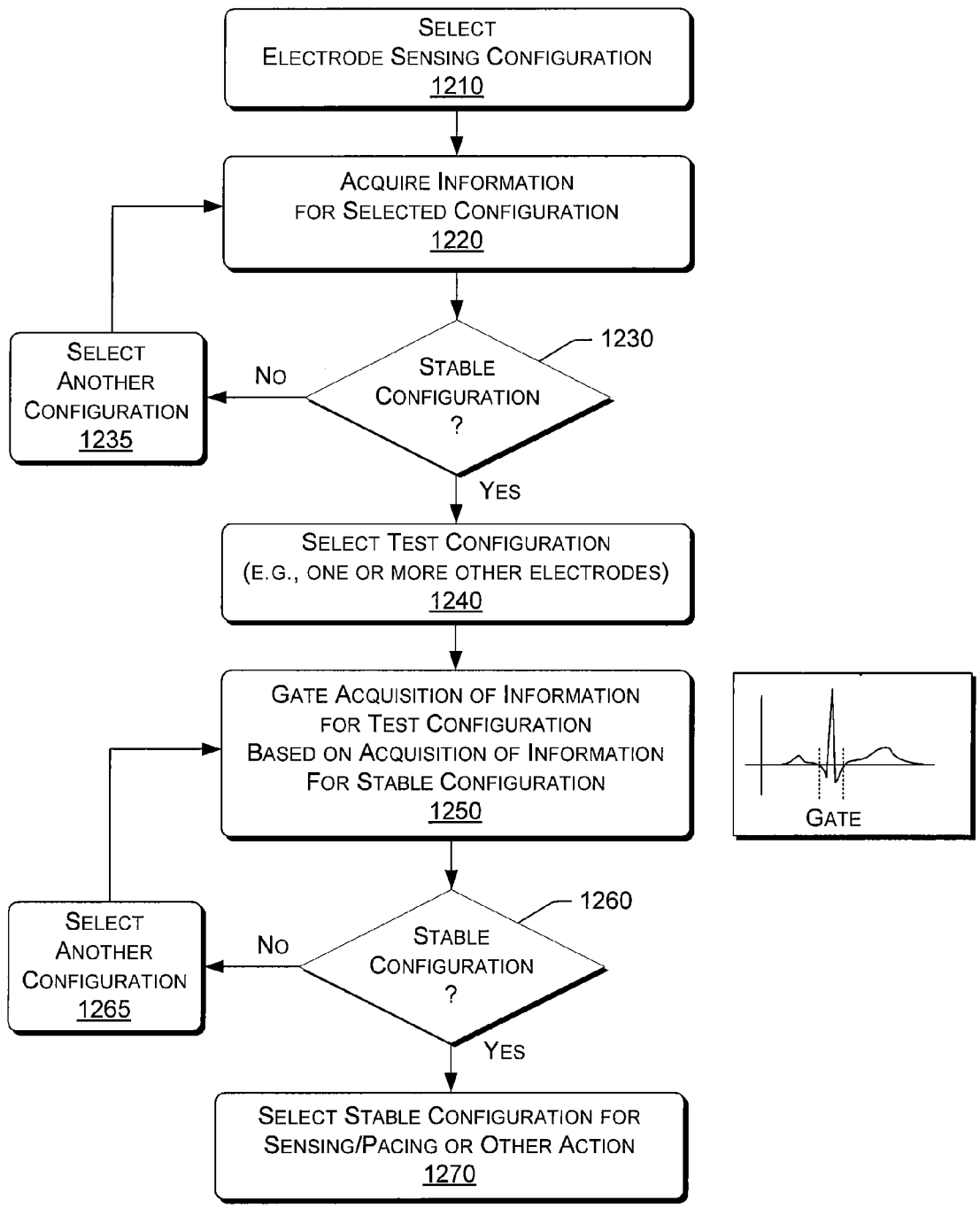
FIG. 12 is a block diagram of an exemplary method for gating acquisition of position information where the gating relies on information sensed using a stable electrode configuration.

FIG. 12 shows an exemplary method 1200 that can determine whether an electrode sensing configuration is suitable for gating acquisition for position information of one or more other electrodes. The method 1200 commences in a selection block 1210 that selects an electrode sensing configuration (e.g., for IEGM acquisition). In an acquisition block 1220, position information is acquired for the selected electrode sensing configuration, for example, using a localization system such as the ENSITE® NAVX® system. The selected electrode sensing configuration may correspond to a unipolar arrangement where one electrode is positioned in the heart and another electrode positioned in or on the body but not in the heart (e.g., an extracardiac electrode). In an alternative scenario, the selected electrode sensing configuration may rely on bipolar or other multipolar sensing.

After the acquisition block 1220, the method 1200 enters a decision block 1230 that decides whether the selected configuration is stable. If the decision block 1230 decides that the selected configuration is not stable, the method 1200 enters a selection block 1235 that selects a different configuration. However, if the decision block 1230 decides that the selected configuration is stable, the method 1200 continues to a selection block 1240 for selection of a test electrode configuration, which may include one or more electrodes that are not part of the selected sensing electrode configuration.

After selection of a test electrode configuration, the method 1200 enters a gated acquisition block 1250 that relies on sensed electrical activity of the heart to gate acquisition of position information for the test electrode configuration (see, e.g., the IEGM with dashed lines indicating a gate). As shown in FIG. 12, a decision block 1260 follows the gated acquisition block 1250 to decide if the selected test electrode configuration is stable. If the decision block 1260 decides that the test electrode configuration is not stable, the method 1200 continues at a selection block 1265 to select another test configuration. Such a selection may or may not require repositioning of a lead when the method 1200 is performed in an intraoperative setting (e.g., acute state). For example, where a lead includes multiple electrodes, the selection block 1265 may select an electrode configuration that includes an electrode that was not part of the unstable test configuration. If repositioning of a lead is required and such repositioning effects the gating (e.g., the previously determined stable sensing electrode configuration), the method 1200 may require a return to the selection block 1210.

In the instance the decision block 1260 decides that the selected test configuration is stable (e.g., according to one or more criteria), the method 1200 continues at a selection block 1270 that may select the stable test electrode configuration, for example, for chronic or other use (e.g., further testing, etc.).

Figure 13:
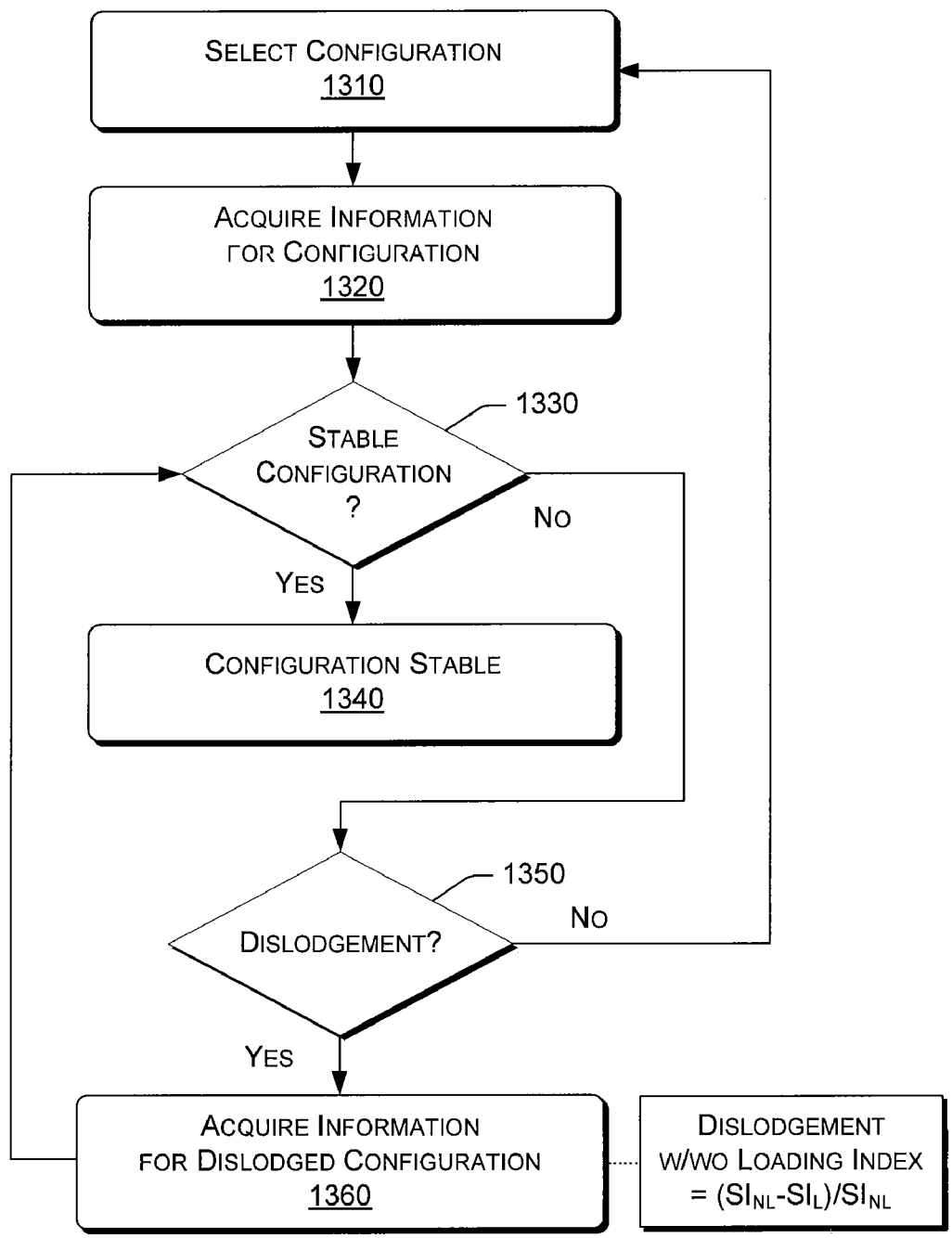
FIG. 13 is a block diagram of an exemplary method for deciding whether dislodgement occurred for a lead or an electrode.

FIG. 13 shows an exemplary method 1300 for addressing dislodgment of an electrode or lead. Specifically, the method 1300 addresses situations where dislodgment may cause an electrode or lead to move to a more stable location. The method 1300 commences in a selection block 1310 where an electrode or lead configuration is selected. An acquisition block 1320 follows that acquires position information for the electrode or one or more electrodes associated with the lead. A decision block 1330 decides, based at least in part on the acquired information, whether the selected configuration is stable (e.g., optionally using one or more stability criteria). If the decision block 1330 decides that the selected configuration is stable, the method 1300 enters a conclusion block 1340 that concludes the selected configuration is stable. During implant of a pacing device (e.g., the device 100 of FIGS. 1 and 2), such a conclusion may be required prior to use of the selected configuration for chronic sensing, pacing, shocking, etc.

In the instance the decision block 1330 decides that the selected configuration is not stable, the method 1300 proceeds to another decision block 1350. The decision block 1350 decides whether dislodgment occurred. For example, a modal analysis of position information may reveal a bi-modal distribution as exhibited in the plot 600 of FIG. 6. A bi-modal distribution may include two position averages (e.g., a first distinct position average for a first set of cardiac cycles and a second distinct position average for a second set of cardiac cycles). Evidence of a bi-modal or other multimodal distribution may indicate dislodgement, especially where data sets or metrics show a correspondence to distinct time frames (e.g., sets of cardiac cycles).

Referring again to the decision block 1350 of FIG. 13, if a decision is made that dislodgment did not occur, the method 1300 returns to the selection block 1310, which may act to select another configuration. However, if the decision block 1350 decides that dislodgement occurred, the method 1300 proceeds to an acquisition block 1360 that acquires position information for the configuration in its current condition, optionally while applying a load. As mentioned, stability may be assessed while applying a load to a lead (e.g., tension or compression at a proximal end, away from the heart). A dislodgement stability index may be calculated, for example, based on the equation: $(SI_{no\ load} - SI_{loaded})/SI_{no\ load}$.

As described herein, an exemplary method may include applying techniques to assess or improve accuracy of a metric such as a stability index. For example, if a pacing algorithm changes pacing rate during acquisition of position information for an electrode, the change can be expected to alter the electrode's trajectory. Further, a change in pacing rate is likely to alter time fiducials in instances where they are used to trigger acquisition of position data. In instances where one or more events (e.g., as noted in an IEGM) are used to gate acquisition of position information, a change in pacing rate may affect relative timing of the events. To increase accuracy, an exemplary method can apply a constant pacing rate that exceeds the intrinsic rate of the heart (e.g., overdrive pacing). Such a technique helps ensure a reproducible position of an electrode at like time points across cardiac cycles.

As described herein, an exemplary method implements overdrive pacing by pacing the heart using a single ventricle or biventricular electrode configuration, noting that a biventricular electrode configuration may inherently provide a more regular pattern of contraction. The selected electrode configuration may correspond to a configuration intended to be used chronically. For example, if biventricular pacing is indicated for a patient, a biventricular electrode configuration can be selected for patient to more closely mimic the chronic state.

FIG. 14 shows an exemplary method 1400 for assessing chronic stability along with a computing device 1430 and one or more databases 1450 and 1460. The method 1400 commences in a selection block 1410 that selects a chronic configuration, which may be an electrode configuration implemented in conjunction with an implanted device to sense, pace or shock the heart. In an alternative example, the electrode configuration may be implemented in conjunction with an implanted device to sense, pace or shock a nerve or other tissue (e.g., vagal nerve, phrenic nerve, diaphragm, etc.). In an acquisition block 1414, position information is acquired. For example, patches may be placed on a patient's body to deliver current where the implanted device senses potentials related to the current. In turn, the sensed potentials may be communicated from the implanted device to an external device such as an implantable device programmer (see, e.g., the telemetry circuit of the device 100 of FIG. 2).

According to the method 1400, a comparison block 1418 compares the acquired chronic state information to information associated with the same configuration in an acute state (e.g., as acquired during an intraoperative procedure) or to information associated with the same configuration in a historic chronic state (e.g., a week earlier, a month earlier, during a post-operative period, etc.). In a conclusions block 1422, the method 1400 may make one or more conclusions based on the comparison of block 1418.

As mentioned, the example of FIG. 14 also shows the computing device 1430 and the databases for acute data 1450 and chronic data 1460. The acute database 1450 may store stability index or other stability metric data for various configurations examined during an acute procedure. For example, for each configuration, the acute database 1450 may store metrics in a relational format along with a stability tolerance (ST). The stability tolerance indicates a tolerable percent deviation for one or more of the metrics as determined in a chronic state. For example, for configuration C1, the stability index sum is 2.4 and the ST is 4%; thus, a chronic state stability index sum of 2.3 or less will exceed the stability tolerance and optionally give rise to an alert. An example of out-of-tolerance stability metrics is shown for C2 in the chronic state data 1460 where $SI_{sum}$, $SI_{mean}$ decreased and $SI_{stddev}$ increased. The method 1400 may be implemented in the form of computer-executable instructions stored in memory, for example, of the computing device 1430, which may be a device programmer configured to store or otherwise access the data of the acute database 1450 or the data of the chronic database 1460.

While the data is shown for individual configurations in the example of FIG. 14, data may be stored additionally or alternatively for leads. For example, stability metrics may be determined and stored for a lead based on position information acquired for one or more individual electrodes of the lead. Further, lead metrics may account for length, electrode spacing, material properties, etc., of a lead. For example, position information or metric(s) for an unanchored tip electrode of a left ventricular lead may be allowed greater tolerance or weighted less than an intermediate electrode of the lead.

According to the method 1400, lead stability can be determined, for example, during an in-clinic follow-up visit. Such a method may rely on telemetric or RF communication between a localization system (e.g., the ENSITE® NAVX® system) and information sensed using electrodes on an implanted lead connected to an implanted device.

An exemplary method includes, at a post-implant follow-up visit, a clinician placing various patches on a patient where the patches carry energy sufficient to generate a localization field within the patient's body. Upon delivery of energy, an implanted device senses signals associated with the delivered energy using one or more electrodes, converts the signals to digital data and then wirelessly communicates the data to an external computing device. The communicated data may be analyzed or stored and analyzed at a later time.

In various exemplary methods, at implant and at subsequent follow-ups visits, relative positions of an electrode associated with a known stable lead (e.g., an RA lead) and an electrode associated with a lead susceptible to instability (e.g., a CS lead) can be noted, for example as the distance between the two electrodes at a fiducial time point. Where more than two electrodes are compared, the angle made between electrodes at a fiducial time point can be noted (e.g., an angle formed between three electrodes). Given such information, one or more exemplary stability indexes can be computed, for example, as a difference in a distance or an angle at one fiducial time point or as a sum or an average of differences at multiple time points. In this exemplary approach, even if localization system patches are not placed in identical location on the body of a patient (e.g., which would cause a shift in absolute positional coordinate values), a chronic stability trend may still be determined, for example, by using a stable reference point within the heart.

As described herein, data acquired for a stable heart rhythm with a somewhat varying rate (e.g., within specified normal limits of deviation) may be corrected by normalizing common time points to duration of each cardiac cycle. For example, an acquisition system may sample an electrode position in tenths or other fractions of a cardiac cycle rather than according to a set interval (e.g., every 75 ms). In a more complex manner, sampling may space points according to slope or other features, for example, to more accurately sample a QRS complex. An exemplary technique may optionally, for intrinsic or paced cycles, rely on ECG or IEGM morphology as a prerequisite for inclusion of data from a beat (e.g., cardiac cycle) in a stability index calculation. Such an approach can act to filter out or exclude data from beats having certain types of morphology such as PVC morphology.

In various instances, depending on placement of electrodes that generate a localization field, respiration may affect accuracy of position data. For example, referring to FIG. 5, as a patient breathes, the torso changes shape, which can alter the alignment of the electrodes 522, 522', 524, 524', 526, 526' and 528. Further, as respiration introduces air into the body, dielectric properties of media between electrodes of a directional pair may change. To account for the affects of respiration, an exemplary data acquisition technique may include an algorithm that compensates for respiratory motion. Alternatively, compensation of filtering may be performed after data acquisition, for example, using one or more algorithms that identify frequencies in data that are likely related to respiration and adjust the data (e.g., filter or normalize) to compensate for respiration. In other instances, respiration gating may be used during data acquisition, for example, akin to techniques used during acquisition of nuclear magnetic resonance data (e.g., NMR or MRI data). For example, beats to be included in a stability index metric may be gated to a particular portion of the respiratory cycle.

The ENSITE® NAVX® system includes a so-called "RespComp" algorithm that uses a combination of impedance between various pairs of patches, which create the localization field, as a measure of respiratory motion. In yet another alternative, motion of electrodes that are known to be stable can be used to ascertain respiratory motion. For example, position data with respect to time may have low frequency content (approximately 0.1 Hz to approximately 0.5 Hz) that can be due to respiration, which can be subtracted from the motion of the electrode of which stability is of interest.

Instantaneous fluid status, among other variables, can cause some drift in position as measured by a localization system such as the ENSITE® NAVX® system. An exemplary method can include a correction factor that accounts for fluid status drift, which may be found by comparing position of a stable electrode from one cycle to the next and applying any measured offset to an electrode of interest.

As described herein, an exemplary method includes calculating one or more stability metrics for an electrode. For example, an exemplary method includes selecting an electrode located in a patient; acquiring position information with respect to time for the electrode by repeatedly measuring electrical potentials in an electrical localization field established in the patient; calculating a stability metric for the electrode based on the acquired position information with respect to time; mapping the stability metric to a map that includes one or more anatomical features; and, based in part on the mapping, deciding if the selected electrode is in a stable location for sensing biological electrical activity, for delivering electrical energy or for sensing biological electrical activity and delivering electrical energy (e.g., as associated with a cardiac therapy, nerve therapy or other therapy).

In various exemplary methods, acquiring position information with respect to time may include repeatedly measuring electrical potentials over multiple cycles (e.g., cardiac cycles, respiratory cycles, cycles defined by delivering electrical energy to the patient, cycles defined by sensing biological electrical activity, etc.).

As described herein, a stability metric can be a path length metric associated with a cycle, for example, where variation in the path length metric over multiple cycles provides an indication of stability of an electrode as located in the patient. As described herein, a stability metric can be an area metric associated with a cycle, for example, where variation in the area metric over multiple cycles provides an indication of stability of an electrode as located in the patient. As described herein, a stability metric can be a standard deviation metric for multiple cycles that provides an indication of stability of an electrode as located in the patient.

In various examples, fiducials may be used during acquisition of information, for position determinations, or stability metric calculations. For example, a fiducial may be one or more discrete times or time intervals, based on percentages or fractions of a cycle (e.g., a cardiac, respiratory or other cycle), based on one or more events in an electrogram (e.g., an "event fiducial" based on a muscle activity electrogram or a neuroelectrogram).

An exemplary stability metric optionally relies on cycle-to-cycle fiducial-associated position differentials for positions of the electrode over multiple cycles. For example, a stability metric may be a stability index sum that divides a sum of the position differentials by number of cycles. In another example, a stability metric may be a stability index mean that divides a sum of the position differentials by number of cycles and by number of fiducials per cycle.

As described herein, an exemplary method can include, during some or all cycles, delivering energy to a patient via a lead or a catheter positioned in the patient. Such a method may include calculating a stability metric for cycles associated with delivery of energy and calculating a stability metric for the cycles not associated with delivery of energy. For example, a method can include intrinsic cardiac cycles and paced cardiac cycles and associated intrinsic and paced stability metrics. With respect to pacing, a method may include acquiring position information with respect to time during paced activation of the heart at an overdrive pacing rate.

As described herein, various techniques can be used to improve accuracy of a stability metric. For example, a method may include sensing biological electrical activity and, prior to calculating a stability metric, excluding at least some acquired position information for a selected electrode based on the sensed biological electrical activity. In another example, a method may include filtering position information to remove respiratory motion, filtering position information to remove drift artifact or the like.

As described herein, one or more exemplary computer-readable storage media can include processor-executable instructions to configure a computing device to: select an electrode located in a patient based upon user input; acquire position information with respect to time for the electrode by repeatedly measuring electrical potentials in an electrical localization field established in the patient; calculate a stability metric for the electrode based on the acquired position information with respect to time; map the stability metric to a map that includes one or more anatomical features; and, based in part on the map, decide if the selected electrode is in a stable location for sensing biological electrical activity, for delivering electrical energy or for sensing biological electrical activity and delivering electrical energy.

As described herein, an exemplary system can include one or more processors; memory; and control logic configured to: select an electrode located in a patient; acquire position information with respect to time for the electrode by repeatedly measuring electrical potentials in an electrical localization field established in the patient; calculate a stability metric for the electrode based on the acquired position information with respect to time; map the stability metric to a map that includes one or more anatomical features; and, based in part on the map, decide if the selected electrode is in a stable location for sensing biological electrical activity, for delivering electrical energy or for sensing biological electrical activity and delivering electrical energy. Such control logic may be stored as instructions on one or more computer-readable media (e.g., memory) and/or be implemented by one or more devices (e.g., an implanted device and an external device).

Where an exemplary method includes intrinsic and paced activation of the heart (see, e.g., FIG. 11), such a method may include selecting an electrode located in a patient; during intrinsic activation of the heart, acquiring position information with respect to time for the electrode by repeatedly measuring electrical potentials in an electrical localization field established in the patient; during paced activation of the heart, acquiring position information with respect to time for the electrode by repeatedly measuring electrical potentials in an electrical localization field established in the patient; calculating an intrinsic activation stability metric for the electrode based on the acquired position information with respect to time during the intrinsic activation of the heart; calculating a paced activation stability metric for the electrode based on the acquired position information with respect to time during the paced activation of the heart; and comparing the intrinsic activation stability metric to the paced activation stability metric to decide whether the electrode, as located in the patient, is in a stable location for delivery of a therapy that includes paced activation of the heart. Such a method can further include mapping the intrinsic activation stability metric and the paced activation stability metric to a map (e.g., a map that includes one or more anatomical features).

As described herein, a method may include calculating an intrinsic-paced stability differential based on an intrinsic activation stability metric and a paced activation stability metric. For example, where the stability metric is a path length metric, a differential may be a distance, where the stability metric is an area metric, a differential may be an area and where a stability metric is a standard deviation or other statistical parameter, a differential may be a difference between two such parameters. Further, a differential may be mapped to a map (e.g., a map that includes one or more anatomical features).

As described herein, an exemplary system can include one or more processors; memory; and control logic configured to: select an electrode located in a patient; during intrinsic activation of the heart, acquire position information with respect to time for the electrode by repeatedly measuring electrical potentials in an electrical localization field established in the patient; during paced activation of the heart, acquire position information with respect to time by repeatedly measuring electrical potentials in an electrical localization field established in the patient; calculate an intrinsic activation stability metric for the electrode based on the acquired position information with respect to time during the intrinsic activation of the heart; calculate a paced activation stability metric for the electrode based on the acquired position information with respect to time during the paced activation of the heart; and compare the intrinsic activation stability metric to the paced activation stability metric to decide whether the electrode, as located in the patient, is in a stable location for delivery of a therapy that includes paced activation of the heart. Such control logic may be stored as instructions on one or more computer-readable media (e.g., memory) and/or be implemented by one or more devices (e.g., an implanted device and an external device).

As described herein, an exemplary method may include loading of a lead or catheter (see, e.g., FIG. 13). Such an exemplary method can include selecting an electrode located in a patient where the electrode is a lead-based electrode; acquiring position information with respect to time for the electrode by repeatedly measuring electrical potentials in an electrical localization field established in the patient; during application of force to the lead, acquiring position information with respect to time for the electrode by repeatedly measuring electrical potentials in an electrical localization field established in the patient; calculating an unloaded stability metric for the electrode based on the acquired position information with respect to time; calculating a loaded stability metric for the electrode based on the acquired position information with respect to time during the application of force to the lead; and comparing the unloaded stability metric to the loaded stability metric to decide whether the electrode, as located in the patient, is in a stable location for delivery of a therapy. Such a method may also include mapping the unloaded stability metric and the loaded stability metric to a map (e.g., a map that includes one or more anatomical features). Such a method may include sensing biological electrical activity, paced activation of the heart, nerve stimulation, muscle stimulation, etc.

A method that includes loading a lead or a catheter may include calculating an unloaded-loaded stability differential based on an unloaded stability metric and a loaded activation stability metric. For example, where the stability metric is a path length metric, a differential may be a distance, where the stability metric is an area metric, a differential may be an area and where a stability metric is a standard deviation or other statistical parameter, a differential may be a difference between two such parameters. Further, a differential may be mapped to a map (e.g., a map that includes one or more anatomical features).

As described herein, an exemplary system can include one or more processors; memory; and control logic configured to: select an electrode located in a patient where the electrode is a lead-based electrode; acquire position information with respect to time for the electrode by repeatedly measuring electrical potentials in an electrical localization field established in the patient; during application of force to the lead, acquire position information with respect to time for the electrode by using the electrode for repeatedly measuring electrical potentials in an electrical localization field established in the patient; calculate an unloaded stability metric for the electrode based on the acquired position information with respect to time; calculate a loaded stability metric for the electrode based on the acquired position information with respect to time during the application of force to the lead; and compare the unloaded stability metric to the loaded stability metric to decide whether the electrode, as located in the patient, is in a stable location for delivery of a therapy. Such control logic may be stored as instructions on one or more computer-readable media (e.g., memory) and/or be implemented by one or more devices (e.g., an implanted device and an external device).

As described herein, an exemplary method may perform stability determinations in association with gated acquisition of information (see, e.g., FIG. 12). For example, an exemplary method can include selecting an electrode located in a patient; acquiring position information with respect to time for the electrode by repeatedly measuring electrical potentials in an electrical localization field established in the patient; calculating a stability metric for the electrode based on the acquired position information with respect to time; deciding if the selected electrode, as located in the patient, is in a stable location for sensing cardiac electrical activity; and, if the deciding decides that the selected electrode is in a stable location for sensing cardiac electrical activity, selecting a different electrode located in the patient, sensing cardiac electrical activity using the electrode at the stable location, gating acquisition of position information for the different electrode based on the sensed cardiac electrical activity, calculating a stability metric for the different electrode, and deciding if the different electrode, as located in the patient, is in a stable location for use in a cardiac therapy. Such a method may include delivering energy to the heart using either or both of the electrodes. In a particular example, a cardiac therapy may include use of the electrode for sensing biological electrical activity and use of the different electrode for paced activation of the heart. Such a method may further include mapping the stability metrics to a map (e.g., a map that includes one or more anatomical features).

In the foregoing method, a stability metric for the electrode or the different electrode may be a path length metric associated with a cycle, for example, where variation in the path length metric over multiple cycles provides an indication of stability of an electrode as located in the patient. In another example, a stability metric for the electrode or the different electrode may be an area metric associated with a cycle, for example, where variation in the area metric over multiple cycles provides an indication of stability of an electrode as located in the patient. In yet another example, a stability metric for the electrode or the different electrode may be a standard deviation metric for multiple cycles, for example, that provides an indication of stability of an electrode as located in the patient.

As described herein, an exemplary system can include one or more processors; memory; and control logic configured to: select an electrode located in a patient; acquire position information with respect to time for the electrode by repeatedly measuring electrical potentials in an electrical localization field established in the patient; calculate a stability metric for the electrode based on the acquired position information with respect to time; decide if the selected electrode, as located in the patient, is in a stable location for sensing cardiac electrical activity; and, in response to a decision that the selected electrode is in a stable location for sensing cardiac electrical activity to select a different electrode located in the patient, sense cardiac electrical activity using the electrode at the stable location, gate acquisition of position information for the different electrode based on the sensed cardiac electrical activity, calculate a stability metric for the different electrode, and decide if the different electrode, as located in the patient, is in a stable location for use in a cardiac therapy. Such control logic may be stored as instructions on one or more computer-readable media (e.g., memory) and/or be implemented by one or more devices (e.g., an implanted device and an external device).

As described herein, an exemplary method can include calculation of stability metrics for acute and chronic scenarios (see, e.g., FIG. 14). For example, exemplary method can include selecting an electrode located in a patient; during an intraoperative, acute state, acquiring position information with respect to time for the electrode by repeatedly measuring electrical potentials in an electrical localization field established in the patient; during a post-operative, chronic state, acquiring position information with respect to time for the electrode by repeatedly measuring electrical potentials in an electrical localization field established in the patient; calculating an acute state stability metric for the electrode based on the acquired position information with respect to time during the acute state; calculating a chronic state stability metric for the electrode based on the acquired position information with respect to time during the chronic state; and comparing the acute state stability metric to the chronic state stability metric to decide whether the electrode, as located in the patient in the chronic state, is in a stable location for delivery of a therapy. Such a method may include mapping the acute state stability metric and the chronic state stability metric to a map (e.g., a map that includes one or more anatomical features).

A method that acquires acute and chronic state information may include calculating an acute state-chronic state stability differential based on an acute state stability metric and a chronic state stability metric. For example, where the stability metric is a path length metric, a differential may be a distance, where the stability metric is an area metric, a differential may be an area and where a stability metric is a standard deviation or other statistical parameter, a differential may be a difference between two such parameters. Further, a differential may be mapped to a map (e.g., a map that includes one or more anatomical features).

As described herein, an exemplary can include one or more processors; memory; and control logic configured to: select an electrode located in a patient; during an intraoperative, acute state, acquire position information with respect to time for the electrode by repeatedly measuring electrical potentials in an electrical localization field established in the patient; during a post-operative, chronic state, acquire position information with respect to time for the electrode by repeatedly measuring electrical potentials in an electrical localization field established in the patient; calculate an acute state stability metric for the electrode based on the acquired position information with respect to time during the acute state; calculate a chronic state stability metric for the electrode based on the acquired position information with respect to time during the chronic state; and compare the acute state stability metric to the chronic state stability metric to decide whether the electrode, as located in the patient in the chronic state, is in a stable location for delivery of a therapy. Such control logic may be stored as instructions on one or more computer-readable media (e.g., memory) and/or be implemented by one or more devices (e.g., an implanted device and an external device).

As described herein, an exemplary method may include comparing current chronic state information to historic chronic state information (see, e.g., FIG. 14). For example, an exemplary method can include selecting a chronically implanted electrode located in a patient; acquiring position information with respect to time for the electrode by repeatedly measuring electrical potentials in an electrical localization field established in the patient; calculating a stability metric for the electrode based on the acquired position information with respect to time; and comparing the stability metric to a previously calculated stability metric for the selected electrode to decide whether stability of the chronically implanted electrode, as located in the patient, has changed. Such a method may further include mapping the stability metric and the previously calculated stability metric to a map (e.g., a map that includes one or more anatomical features).

A method that acquires chronic state information over time may include calculating a chronic state-chronic state stability differential based on a current chronic state stability metric and a historic chronic state stability metric. For example, where the stability metric is a path length metric, a differential may be a distance, where the stability metric is an area metric, a differential may be an area and where a stability metric is a standard deviation or other statistical parameter, a differential may be a difference between two such parameters. Further, a differential may be mapped to a map (e.g., a map that includes one or more anatomical features).

As described herein, an exemplary system can include one or more processors; memory; and control logic configured to: select a chronically implanted electrode located in a patient; acquire position information with respect to time for the electrode by repeatedly measuring electrical potentials in an electrical localization field established in the patient; calculate a stability metric for the electrode based on the acquired position information with respect to time; and compare the stability metric to a previously calculated stability metric for the selected electrode to decide whether stability of the chronically implanted electrode, as located in the patient, has changed. Such control logic may be stored as instructions on one or more computer-readable media (e.g., memory) and/or be implemented by one or more devices (e.g., an implanted device and an external device).

Various exemplary techniques may include deriving a lead stability metric to more effectively place coronary sinus leads. As described herein, a stability metric may be a stability index computed as the distance between an electrode location at a fiducial time point for two different cardiac cycles, a stability index computed as the sum or the mean of distances between respective electrode locations at more than one fiducial or relative time point of different cardiac cycles.

As described herein, a stability metric may be computed as the standard deviation of path length or area enclosed by a swept electrode trajectory over the course of each of several cardiac cycles. A stability metric may be optionally measured in a point-by-point manner by moving a lead or catheter to various location, for example, where a value of the stability index is encoded along a color scale and displayed on a map at each respective anatomic location.

With respect to data analysis, ECG, IEGM or other biosignal morphology may be used to exclude information associated with inconsistent beats or other artifacts from a calculation of a stability metric. Various methods may optionally use filtering to remove artifacts such as respiratory motion or drift from a location signal prior to calculating a stability metric.

With respect to chronic electrode stability, an exemplary method may include tracking at finite intervals by noting relative positions (distance, angle) of two or more electrodes, for example, where at least one landmark or electrode is known or assumed to be stable.

Exemplary External Programmer

Figure 15:
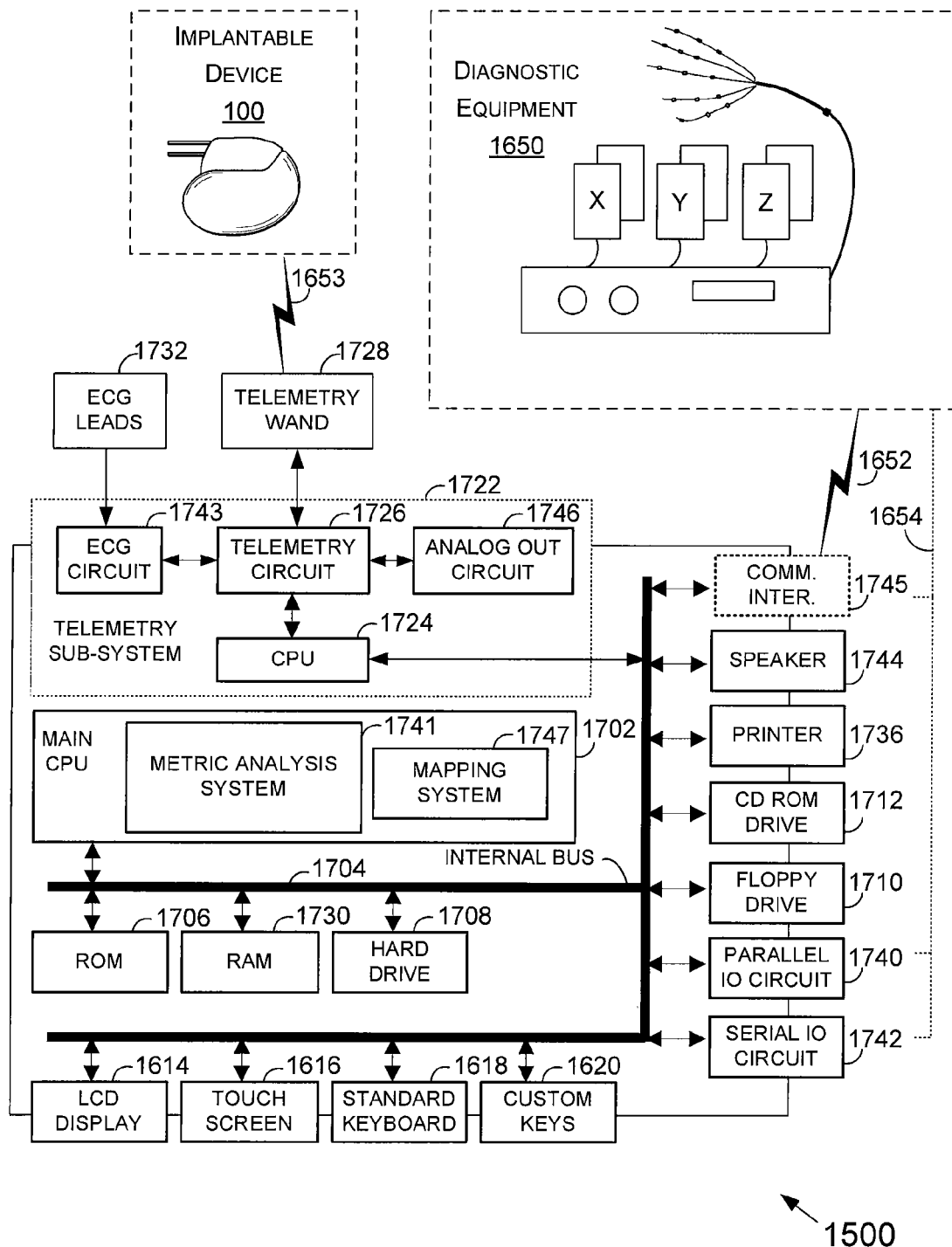
FIG. 15 is an exemplary system for acquiring information and analyzing information to assess stability of an electrode, a lead or implanted device.

FIG. 15 illustrates pertinent components of an external programmer 1500 for use in programming an implantable medical device 100 (see, e.g., FIGS. 1 and 2). The external programmer 1500 optionally receives information from other diagnostic equipment 1650, which may be a computing device capable of acquiring location information and other information. For example, the equipment 1650 may include a computing device to deliver current and to measure potentials using a variety of electrodes including at least one electrode positionable in the body (e.g., in a vessel, in a chamber of the heart, within the pericardium, etc.). Equipment may include a lead for chronic implantation or a catheter for temporary implantation in a patient's body. Equipment may allow for acquisition of respiratory motion and aid the programmer 1500 in distinguishing respiratory motion from cardiac.

Briefly, the programmer 1500 permits a clinician or other user to program the operation of the implanted device 100 and to retrieve and display information received from the implanted device 100 such as IEGM data and device diagnostic data. Where the device 100 includes a module such as the position detection module 239, then the programmer 1500 may instruct the device 100 to measure potentials and to communicate measured potentials to the programmer via a communication link 1653. The programmer 1500 may also instruct a device or diagnostic equipment to deliver current to generate one or more potential fields within a patient's body where the implantable device 100 may be capable of measuring potentials associated with the field(s).

The external programmer 1500 may be configured to receive and display ECG data from separate external ECG leads 1732 that may be attached to the patient. The programmer 1500 optionally receives ECG information from an ECG unit external to the programmer 1500. As already mentioned, the programmer 1500 may use techniques to account for respiration.

Depending upon the specific programming, the external programmer 1500 may also be capable of processing and analyzing data received from the implanted device 100 and from ECG leads 1732 to, for example, render diagnosis as to medical conditions of the patient or to the operations of the implanted device 100. As noted, the programmer 1500 is also configured to receive data representative of conduction time delays from the atria to the ventricles and to determine, therefrom, an optimal or preferred location for pacing. Further, the programmer 1500 may receive information such as ECG information, IEGM information, information from diagnostic equipment, etc., and determine one or more metric (e.g., consider the method 300).

Now, considering the components of programmer 1500, operations of the programmer are controlled by a CPU 1702, which may be a generally programmable microprocessor or microcontroller or may be a dedicated processing device such as an application specific integrated circuit (ASIC) or the like. Software instructions to be performed by the CPU are accessed via an internal bus 1704 from a read only memory (ROM) 1706 and random access memory 1730. Additional software may be accessed from a hard drive 1708, floppy drive 1710, and CD ROM drive 1712, or other suitable permanent or removable mass storage device. Depending upon the specific implementation, a basic input output system (BIOS) is retrieved from the ROM 1706 by CPU 1702 at power up. Based upon instructions provided in the BIOS, the CPU 1702 "boots up" the overall system in accordance with well-established computer processing techniques.

Once operating, the CPU 1702 displays a menu of programming options to the user via an LCD display 1614 or other suitable computer display device. To this end, the CPU 1702 may, for example, display a menu of specific programming parameters of the implanted device 100 to be programmed or may display a menu of types of diagnostic data to be retrieved and displayed. In response thereto, the clinician enters various commands via either a touch screen 1616 overlaid on the LCD display or through a standard keyboard 1618 supplemented by additional custom keys 1620, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

With regard to the determination of location stability (e.g., for pacing, sensing, etc.), CPU 1702 includes a metric analysis system 1741 and a 3-D mapping system 1747. The systems 1741 and 1747 may receive information from the implantable device 100 and/or diagnostic equipment 1650. The parameter analysis system 1741 optionally includes control logic to associate information and to make one or more conclusions based on a map of a metric or metrics (e.g., consider the block 330 of FIG. 3).

Where information is received from the implanted device 100, a telemetry wand 1728 may be used. Other forms of wireless communication exist as well as forms of communication where the body is used as a "wire" to communicate information from the implantable device 100 to the programmer 1500.

If information is received directly from diagnostic equipment 1650, any appropriate input may be used, such as parallel IO circuit 1740 or serial IO circuit 1742. Motion information received via the device 100 or via other diagnostic equipment 1650 may be analyzed using the mapping system 1747. In particular, the mapping system 1747 (e.g., control logic) may identify positions within the body of a patient and associate such positions with one or more electrodes where such electrodes may be capable of delivering stimulation energy to the heart.

A communication interface 1745 optionally allows for wired or wireless communication with diagnostic equipment 1650 or other equipment. The communication interface 1745 may be a network interface connected to a network (e.g., intranet, Internet, etc.).

A map or model of cardiac motion may be displayed using display 1614 based, in part, on 3-D heart information and optionally 3-D torso information that facilitates interpretation of motion information. Such 3-D information may be input via ports 1740, 1742, 1745 from, for example, a database, a 3-D imaging system, a 3-D location digitizing apparatus (e.g., stereotactic localization system with sensors and/or probes) capable of digitizing the 3-D location. According to such an example, a clinician can thereby view the stability of a location on a map of the heart to ensure that the location is acceptable before an electrode or electrodes are positioned and optionally fixed at that location. While 3-D information and localization are mentioned, information may be provided with fewer dimensions (e.g., 1-D or 2-D). For example, where motion in one dimension is insignificant to one or more other dimensions, then fewer dimensions may be used, which can simplify procedures and reduce computing requirements of a programmer, an implantable device, etc. The programmer 1500 optionally records procedures and allows for playback (e.g., for subsequent review). For example, a heart map and all of the electrical activation data, mechanical activation data, parameter data, etc., may be recorded for subsequent review, perhaps if an electrode needs to be repositioned or one or more other factors need to be changed (e.g., to achieve an optimal configuration). Electrodes may be lead based or non-lead based, for example, an implantable device may operate as an electrode and be self powered and controlled or be in a slave-master relationship with another implantable device (e.g., consider a satellite pacemaker, etc.). An implantable device may use one or more epicardial electrodes.

Once all pacing leads are mounted and all pacing devices are implanted (e.g., master pacemaker, satellite pacemaker, biventricular pacemaker), the various devices are optionally further programmed.

The telemetry subsystem 1722 may include its own separate CPU 1724 for coordinating the operations of the telemetry subsystem. In a dual CPU system, the main CPU 1702 of programmer communicates with telemetry subsystem CPU 1724 via internal bus 1704. Telemetry subsystem additionally includes a telemetry circuit 1726 connected to telemetry wand 1728, which, in turn, receives and transmits signals electromagnetically from a telemetry unit of the implanted device. The telemetry wand is placed over the chest of the patient near the implanted device 100 to permit reliable transmission of data between the telemetry wand and the implanted device.

Typically, at the beginning of the programming session, the external programming device 1500 controls the implanted device(s) 100 via appropriate signals generated by the telemetry wand to output all previously recorded patient and device diagnostic information. Patient diagnostic information may include, for example, motion information (e.g., cardiac, respiratory, etc.) recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like.

Data retrieved from the implanted device(s) 100 can be stored by external programmer 1500 (e.g., within a random access memory (RAM) 1730, hard drive 1708, within a floppy diskette placed within floppy drive 1710). Additionally, or in the alternative, data may be permanently or semi-permanently stored within a compact disk (CD) or other digital media disk, if the overall system is configured with a drive for recording data onto digital media disks, such as a write once read many (WORM) drive. Where the programmer 1500 has a communication link to an external storage device or network storage device, then information may be stored in such a manner (e.g., on-site database, off-site database, etc.). The programmer 1500 optionally receives data from such storage devices.

A typical procedure may include transferring all patient and device diagnostic data stored in an implanted device 100 to the programmer 1500. The implanted device(s) 100 may be further controlled to transmit additional data in real time as it is detected by the implanted device(s) 100, such as additional motion information, IEGM data, lead impedance data, and the like. Additionally, or in the alternative, telemetry subsystem 1722 receives ECG signals from ECG leads 1732 via an ECG processing circuit 1743. As with data retrieved from the implanted device 100, signals received from the ECG leads are stored within one or more of the storage devices of the programmer 1500. Typically, ECG leads output analog electrical signals representative of the ECG. Accordingly, ECG circuit 1743 includes analog to digital conversion circuitry for converting the signals to digital data appropriate for further processing within programmer 1500. Depending upon the implementation, the ECG circuit 1743 may be configured to convert the analog signals into event record data for ease of processing along with the event record data retrieved from the implanted device. Typically, signals received from the ECG leads 1732 are received and processed in real time.

Thus, the programmer 1500 is configured to receive data from a variety of sources such as, but not limited to, the implanted device 100, the diagnostic equipment 1650 and directly or indirectly via external ECG leads (e.g., subsystem 1722 or external ECG system). The diagnostic equipment 1650 includes wired 1654 and/or wireless capabilities 1652 which optionally operate via a network that includes the programmer 1500 and the diagnostic equipment 1650 or data storage associated with the diagnostic equipment 1650.

Data retrieved from the implanted device(s) 100 typically includes parameters representative of the current programming state of the implanted devices. Under the control of the clinician, the external programmer displays the current programming parameters and permits the clinician to reprogram the parameters. To this end, the clinician enters appropriate commands via any of the aforementioned input devices and, under control of CPU 1702, the programming commands are converted to specific programming parameters for transmission to the implanted device 100 via telemetry wand 1728 to thereby reprogram the implanted device 100 or other devices, as appropriate.

Prior to reprogramming specific parameters, the clinician may control the external programmer 1500 to display any or all of the data retrieved from the implanted device 100, from the ECG leads 1732, including displays of ECGs, IEGMs, statistical patient information (e.g., via a database or other source), diagnostic equipment 1650, etc. Any or all of the information displayed by programmer may also be printed using a printer 1736.

A wide variety of parameters may be programmed by a clinician. In particular, for CRT, the AV delay and the VV delay of the implanted device(s) 100 are set to optimize cardiac function. In one example, the VV delay is first set to zero while the AV delay is adjusted to achieve the best possible cardiac function, optionally based on motion information. Then, W delay may be adjusted to achieve still further enhancements in cardiac function.

Programmer 1500 optionally includes a modem to permit direct transmission of data to other programmers via the public switched telephone network (PSTN) or other interconnection line, such as a T1 line or fiber optic cable. Depending upon the implementation, the modem may be connected directly to internal bus 1704 may be connected to the internal bus via either a parallel port 1740 or a serial port 1742.

Other peripheral devices may be connected to the external programmer via the parallel port 1740, the serial port 1742, the communication interface 1745, etc. Although one of each is shown, a plurality of input output (IO) ports might be provided. A speaker 1744 is included for providing audible tones to the user, such as a warning beep in the event improper input is provided by the clinician. Telemetry subsystem 1722 additionally includes an analog output circuit 1746 for controlling the transmission of analog output signals, such as IEGM signals output to an ECG machine or chart recorder.

With the programmer 1500 configured as shown, a clinician or other user operating the external programmer is capable of retrieving, processing and displaying a wide range of information received from the ECG leads 1732, from the implanted device 100, the diagnostic equipment 1650, etc., and to reprogram the implanted device 100 or other implanted devices if needed. The descriptions provided herein with respect to FIG. 15 are intended merely to provide an overview of the operation of programmer and are not intended to describe in detail every feature of the hardware and software of the device and is not intended to provide an exhaustive list of the functions performed by the device.

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A method comprising:
   selecting an electrode located in a patient;
   acquiring position information with respect to time for the electrode wherein the position information comprises physical location measurements in one or more dimensions, and the acquiring further comprises using the electrode for repeatedly measuring electrical potentials in an electrical localization field established in the patient;
   calculating a stability metric for the electrode based on the acquired position information with respect to time and further based on the electrical potentials;
   mapping the stability metric to a map that comprises one or more anatomical features; and
   based in part on the mapping, deciding if the selected electrode comprises a stable location for sensing biological electrical activity, for delivering electrical energy or for sensing biological electrical activity and delivering electrical energy.

2. The method of claim 1 wherein the sensing biological electrical activity and the delivering electrical energy are associated with a cardiac therapy.

3. The method of claim 1 wherein the sensing biological electrical activity comprises sensing electrical nerve activity.

4. The method of claim 1 wherein the delivering electrical energy comprises delivering electrical energy to one or more nerves.

5. The method of claim 1 wherein the acquiring position information with respect to time for the electrode comprises repeatedly measuring the electrical potentials over multiple cycles.

6. The method of claim 5 wherein the multiple cycles comprise cardiac cycles.

7. The method of claim 5 wherein the multiple cycles comprise respiratory cycles.

8. The method of claim 5 wherein the multiple cycles comprise cycles defined by delivering electrical energy to the patient.

9. The method of claim 5 wherein the multiple cycles comprise cycles defined by sensing biological electrical activity.

10. The method of claim 5 wherein the stability metric comprises a path length metric associated with a cycle and wherein variation in the path length metric over the multiple cycles provides an indication of stability of the selected electrode as located in the patient.

11. The method of claim 5 wherein the stability metric comprises an area metric associated with a cycle and wherein variation in the area metric over the multiple cycles provides an indication of stability of the selected electrode as located in the patient.

12. The method of claim 5 wherein the stability metric comprises a standard deviation metric for the multiple cycles and provides an indication of stability of the selected electrode as located in the patient.

13. The method of claim 5 wherein for each of the multiple cycles, the acquiring acquires position information associated with fiducials.

14. The method of claim 13 wherein the fiducials comprise one or more discrete times or time intervals.

15. The method of claim 13 wherein the stability metric relies on cycle-to-cycle fiducial-associated position differentials for positions of the electrode over the multiple cycles.

16. The method of claim 15 wherein the stability metric comprises a stability index sum that divides a sum of the position differentials by number of cycles.

17. The method of claim 15 wherein the stability metric comprises a stability index mean that divides a sum of the position differentials by number of cycles and by number of fiducials per cycle.

18. The method of claim 1 further comprising selecting a different electrode located in the patient at a different location and repeating the acquiring, calculating, mapping and deciding for the different electrode at the different location.

19. The method of claim 18 further comprising mapping to a map, which comprises one or more anatomical features, the stability metric for the selected electrode and the stability metric for the selected different electrode.

20. The method of claim 5 further comprising, during some of the multiple cycles, delivering energy to the patient via a lead or a catheter positioned in the patient.

21. The method of claim 20 further comprising calculating a stability metric for the cycles associated with the delivering energy and calculating a stability metric for the cycles not associated with the delivering energy.

22. The method of claim 21 wherein the cycles comprise cardiac cycles and wherein the delivering energy comprises delivering energy to pace the heart.

23. The method of claim 1 wherein the acquiring position information with respect to time occurs during paced activation of the heart at an overdrive pacing rate.

24. The method of claim 1 further comprising sensing biological electrical activity and, prior to the calculating, excluding at least some acquired position information for the selected electrode based on the sensed biological electrical activity.

25. A system comprising:
   one or more processors;
   memory; and
   control logic configured to:
      select an electrode located in a patient;
      acquire position information with respect to time for the electrode and further measure electrical potentials in an electrical localization field established in the patient, wherein the position information comprises physical location measurements in one or more dimensions;
      calculate a stability metric for the electrode based on the acquired position information with respect to time and further based on the electrical potentials;
      map the stability metric to a map that comprises one or more anatomical features; and
      based in part on the map, decide if the selected electrode comprises a stable location for sensing biological electrical activity, for delivering electrical energy or for sensing biological electrical activity and delivering electrical energy.

* * * * *